US006333307B1

(12) United States Patent
Blaschuk et al.

(10) Patent No.: US 6,333,307 B1
(45) Date of Patent: Dec. 25, 2001

(54) COMPOUNDS AND METHOD FOR MODULATING NEURITE OUTGROWTH

(75) Inventors: Orest W. Blaschuk, Westmount; Barbara J. Gour, Montreal, both of (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/250,059

(22) Filed: Feb. 12, 1999

Related U.S. Application Data

(63) Continuation-in-part of application No. 09/115,395, filed on Jul. 14, 1998, which is a continuation-in-part of application No. 08/996,679, filed on Dec. 23, 1997, now Pat. No. 6,169,071, which is a continuation-in-part of application No. 08/893,534, filed on Jul. 11, 1997, now Pat. No. 6,031,072.
(60) Provisional application No. 60/021,612, filed on Jul. 12, 1996.

(51) Int. Cl.$^7$ ............................. A61K 38/12; A61K 38/00
(52) U.S. Cl. .................................. 514/9; 514/11; 530/317; 435/7.1
(58) Field of Search ........................ 514/9, 11; 530/317; 435/7.1

(56) References Cited

U.S. PATENT DOCUMENTS

| | | | |
|---|---|---|---|
| 5,231,082 | 7/1993 | Schasteen | 514/11 |
| 5,352,667 | 10/1994 | Lider et al. | 514/19 |
| 5,510,628 | 4/1996 | Georger, Jr. et al. | 257/32 |
| 5,585,351 | 12/1996 | Ranscht | 514/12 |
| 5,591,432 | 1/1997 | Bronson et al. | 424/130.1 |
| 5,646,250 | 7/1997 | Suzuki | 530/350 |
| 5,665,590 | 9/1997 | Yang | 435/6 |
| 6,031,072 | * 2/2000 | Blaschuk | 530/317 |
| 6,169,071 | * 1/2001 | Blaschuk | 530/317 |

FOREIGN PATENT DOCUMENTS

| | | |
|---|---|---|
| 406 428 B1 | 1/1991 | (EP) . |
| WO 91/04745 | * 4/1991 | (WO) . |
| WO 92/08731 | 5/1992 | (WO) . |
| WO 94/11401 | 5/1994 | (WO) . |
| WO 96/40781 | 12/1996 | (WO) . |
| WO 97/07209 | 2/1997 | (WO) . |
| WO 98/02452 | 1/1998 | (WO) . |
| WO 98/45319 | 10/1998 | (WO) . |

OTHER PUBLICATIONS

Blaschuk et al., "Identification of a Conserved Region Common to Cadherins and Influenza Strain A Hemagglutinins," *J. Mol. Biol. 211*: 670–682, 1990.
Blaschuk et al., "Identification of a Cadherin Cell Adhesion Recognition Sequence," *Developmental Biology 139*: 227–229, 1990.
Lutz et al., "Secondary Structure of the HAV Peptide Which Regulates Cadherin–Cadherin Interaction," *Journal of Biomolecular Structure & Dynamics 13*(3): 447–455, 1995.

Munro and Blaschuk, *Cell Adhesion and Invasion in Cancer Metastasis,* R.G. Landes Company, Austin, TX, 1996, Chapter 3, "The Structure, Function and Regulation of Cadherins," pp. 17–34.
Newton et al., "N–Cadherin Mediates Sertoli Cell–Spermatogenic Cell Adhesion," *Developmental Dynamics 197*: 1–13, 1993.
Overduin et al., "Solution Structure of the Epithelial Cadherin Domain Responsible for Selective Cell Adhesion," *Science 267*: 386–389, 1995.
Redies and Takeichi, "Cadherins in the Developing Central Nervous System: An Adhesive Code for Segmental and Functional Subdivisions," *Developmental Biology 180*: 413–423, 1996.
Willems et al., "Cadherin–dependent cell aggregation is affected by decapeptide derived from rat extracellular superoxide dismutase," *FEBS Letters 363*: 289–292, 1995.
Shapiro et al., "Structural basis of cell–cell adhesion by cadherins," *Nature 374*: 327–337, 1995.
Alexander et al., "An N–Cadherin–Like Protein Contributes to Solute Barrier Maintenance in Cultured Endothelium," *Journal of Cellular Physiology 156*: 610–618, 1993.
Ali et al., "Conformationally Constrained Peptides and Semipeptides Derived from RGD as Potent Inhibitors of the Platelet Fibrinogen Receptor and Platelet Aggregation," *J. Med. Chem. 37*(6): 769–780, 1994.
Blaschuk and Farookhi, "Estradiol Stimulates Cadherin Expression in Rat Granulosa Cells," *Developmental Biology 136*: 564–567, 1989.
Byers et al., "Fibroblast Growth Factor Receptors Contain a Conserved HAV Region Common to Cadherins and Influenza Strain A Hemagglutinins: A Role in Protein–Protein Interactions?," *Developmental Biology 152*: 411–414, 1992.
Craig et al., "Concept and Progress in the Development of RGD–Containing Peptide Pharmaceuticals," *Biopolymers (Peptide Science) 37*: 157–175, 1995.
Letourneau et al., "Interactions of Schwann Cells with Neurites and with Other Schwann Cells Involve the Calcium–dependent Adhesion Molecule, N–cadherin," *Journal of Neurobiology 22*(7): 707–720, 1991.
Samanen et al., "Development of a Small RGD Peptide Fibrinogen Receptor Antagonist with Potent Antiaggregatory Activity in Vitro," *J. Med. Chem. 34*(10): 3114–3125, 1991.
Cardarelli et al., "The Collagen Receptor $\alpha 2\beta 1$, from MG–63 and HT1080 Cells, Interacts with a Cyclic RGD Peptide," *The Journal of Biological Chemistry 267*(32): 23159–23164, 1992.

(List continued on next page.)

Primary Examiner—F. T. Moezie
(74) *Attorney, Agent, or Firm*—Seed Intellectual Property Law Group PLLC

(57) ABSTRACT

Modulating agents comprising cyclic peptides, and compositions comprising such modulating agents are provided. The cyclic peptides comprise a cadherin cell adhesion recognition sequence HAV. Methods for using such peptides and compositions for modulating and/or directing neurite outgrowth in a variety of contexts are also provided.

25 Claims, 21 Drawing Sheets

OTHER PUBLICATIONS

Figure 1:
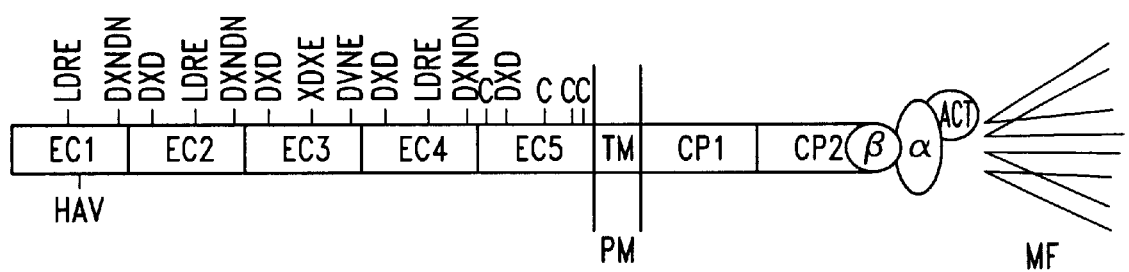

Cepek et al., "Expression of a candidate cadherin in T lymphocytes," *Proc. Natl. Acad. Sci. USA 93:* 6567–6571, 1996.

Doherty and Walsh, "Signal transduction events underlying neurite outgrowth stimulated by cell adhesion molecules," *Current Opinion in Neurobiology 4:* 49–55, 1994.

Laird et al., "Gap Junction Turnover, Intracellular Trafficking, and Phosphorylation of Connexin43 in Brefeldin A–treated Rat Mammary Tumor Cells," *The Journal of Cell Biology 131*(5): 1193–1203, 1995.

Lee et al., "Expression of the Homotypic Adhesion Molecule E–Cadherin by Immature Murine Thymocytes and Thymic Epithelial Cells," *Journal of Immunology 152:* 5653–5659, 1994.

Moran, "The Protein Delivery Service. Advances in technologies for delivering proteins and peptides in therapeutically useful forms," *Pharmaceutical Forum Issue 6:* 4–7, 1996.

Munro et al., "Characterization of Cadherins Expressed by Murine Thymocytes," *Cellular Immunology 169*(Article No. 0123): 309–312, 1996.

Tsuisui et al., "Expression of Cadherin–Catenin Complexes in Human Leukemia Cell Lines," *J. Biochem. 120:* 1034–1039, 1996.

Wiekelgren, "Breaking the Skin Barrier," *PS 12:* 86–88, 1996.

Williams et al., "Activation of the FGF Receptor Underlies Neurite Outgrowth Stimulated by L1, N–CAM, and N–Cadherin," *Neuron 13:* 583–594, 1994.

Blakemore, "Remyelination of CNS axons by Schwann cells transplanted from the sciatic nerve," *Nature 266:* 68–69, 1977.

Bottenstein and Sato, "Growth of a rat neuroblastoma cell line in serum–free supplemented medium," *Proc.Natl. Acad. Sci. USA 76*(1): 514–517, 1979.

Brecknell et al., "Bridge grafts of Fibroblast Growth Factor–4–Secreting Schwannoma Cells Promote Functional Axonal Regeneration in the Nigrostriatal Pathway of the Adult Rat," *Neuroscience 74*(3): 775–784, 1996.

Brockes et al., "Studies on Cultured Rat Schwann Cells. I. Establishment of Purified Populations from Cultures of Peripheral Nerve," *Brain Research 165:* 105–118, 1979.

Brook et al., "Morphology and Migration of Cultured Schwann Cells Transplanted Into the Fimbria and Hippocampus in Adult Rats," *GLIA 9:* 292–304, 1993.

Carlstedt et al., "Nerve Fibre Regeneration Across the PNS–CNS Interface at the Root–Spinal Cord Junction," *Brain Research Bulletin 22:* 93–102, 1989.

Doherty and Walsh, "CAM–FGF Receptor Interactions: A Model for Axonal Growth," *Molecular and Cellular Neuroscience 8*(Article No. 0049): 99–111, 1996.

Duncan et al., "Transplantation of oligodendrocytes and Schwann cells into the spinal cord of the myelin–deficient rat," *Journal of Neurocytology 17:* 351–360, 1988.

Fok–Seang et al., "An analysis of astrocytic cell lines with different abilities to promote axon growth," *Brain Research 689:* 207–223, 1995.

Fok–Seang et al., "Migration of Oligodendrocyte Precursors on Astrocytes and Meningeal Cells," *Developmental Biology 171:* 1–15, 1995.

Franz, "Percutaneous Absorption. On The Relevance Of In Vitro Data," *The Journal of Investigative Dermatology 64*(3): 190–195, 1975.

Franz, "The Finite Dose Technique as a Valid in Vitro Model for the Study of Percutaneous Absorption in Man," *Curr. Probl. Dermatol. 7:* 58–68, 1978.

Ghunikar and Eng, "Astrocyte–Schwann Cell Interactions in Culture," *GLIA 11:* 367–377, 1994.

Irueia–Arispe et al., "Expression of SPARC during Development of the Chicken Cherioallantoic Membrane: Evidence for Regulated Proteolysis In Vivo," *Molecular Biology of the Cell 6:* 327–343, 1995.

Liuzzi and Lasek, "Astrocytes Block Axonal Regeneration in Mammals by Activating the Physiological Stop Pathway," *Science 237:* 642–645, 1987.

McCarthy and Vellis, "Preparation of Separate Astroglial and Oligodendroglial Cell Cultures from Rat Cerebral Tissue," *J. Cell Biology 85:* 890–902, 1980.

Oui, "Angiogenesis Research Offers New Approaches to Treatment of Disease," *Genetic Engineering News,* pp. 15–16, 42, May 1, 1996.

Saffell et al., "Expression of a Dominant Negative FGF Receptor Inhibits Axonal Growth and FGF Receptor Phosphorylation Stimulated by CAMs," *Neuron,* pp. 231–242, Feb. 1995.

Blaschuk et al., "E–Cadherin, estrogens and cancer: is there a connection?" *The Canadian Journal of Oncology 4*(4): 291–301, 1994.

Chuah et al., "Differentiation and survival of rat olfactory epithelial neurons in dissociated cell culture," *Developmental Brain Research 60:* 123–132, 1991.

Doherty et al., "Neurite Outgrowth in Response to Transfected N–CAM and N–Cadherin Reveals Fundamental Differences in Neuronal Responsiveness to CAMS," *Neuron 6:* 247–258, 1991.

Gumbiner et al., "The Role of the Cell Adhesion Molecule Uvomorulin in the Formation and Maintenance of the Epithelial Junctional Complex," *The Journal of Cell Biology 107:* 1575–1587, 1988.

Maksuzaki et al., "cDNAs of Cell Adhesion Molecules of Different Specificity Induce Changes in Cell Shape and Border Formation in Cultured S180 Cells," *The Journal of Cell Biology 110:* 1239–1252, 1990.

Mege et al., "Construction of epithelioid sheets by transfection of mouse sarcoma cells with cDNAs for chicken cell adhesion molecules," *Proc. Natl. Acad. Sci. USA 85:* 7274–7278, 1988.

Nose et al., "Localization of Specificity Determining Sites in Cadherin Cell Adhesion Molecules," *Cell 61:* 147–155, 1990.

Beasley et al., "The post–synaptic density: putative involvement in synapse stabilization vi cadherins and covalent modification by ubiquitination," *Biochemical Society Transactions 23:* 59–64, 1995.

Williams et al., "The Priamary Structure of Hen Ovotransferrin," *Eur. J. Biochem. 122:* 297–303, 1982.

\* cited by examiner

```
human N-cad  DWVIPPINLPENSRGPFPQELVRIRSDRDKNLSLRYSVTGPGADQPPTGIFILNPISGQLSVTKPLDREQ
mouse N-cad  DWVIPPINLPENSRGPFPQELVRIRSDRDKNLSLRYSVTGPGADQPPTGIFILNPISGQLSVTKPLDREL
cow   N-cad  DWVIPPINLPENSRGPFPQELVRIRSDRDKNLSLRYSVTGPGADQPPTGIFIINPISGQLSVTKPLDREL
human P-cad  DWVVAPISVPENGKGPFPQRLNQLKSNKDRDTKIFYSITGPGADSPPEGVFAVEKETGWLLLNKPLDREE
mouse P-cad  EWVMPPIFVPENGKGPFPQRLNQLKSNKDRGTKIFYSITGPGADSPPEGVFTIEKESGWLLLHMPLDREK
human E-cad  DWVIPPISCPENEKGPFPKNLVQIKSNKDKEGKVFYSITGQGADTPPVGVFIIERETGWLKVTEPLDRER
mouse E-cad  DWVIPPISCPENEKGEFPKNLVQIKSNRDKETKVFYSITGQGADKPPVGVFIIERETGWLKVTQPLDREA human N-cad  IARFHLRAHAVDINGNQVENPIDIVINVIDMNDNRPEF
mouse N-cad  IARFHLRAHAVDINGNQVENPIDIVINVIDMNDNRPEF
cow   N-cad  IARFHLRAHAVDINGNQVENPIDIVINVIDMNDNRPEF
human P-cad  IAKYELFGHAVSENGASVEDPMNISIIVTDQNDHKPKF
mouse P-cad  IVKYELYGHAVSENGASVEEPMNISIIVTDQNDNKPKF
human E-cad  IATYTLFSHAVSSNGNAVEDPMEILITVTDQNDNKPEF
mouse E-cad  IAKYILYSHAVSSNGEAVEDPMEIVITVTDQNDNRPEF
```

*Fig. 2*

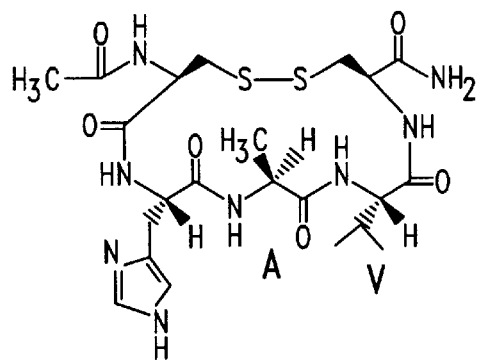
N-Ac-CHAVC-NH₂
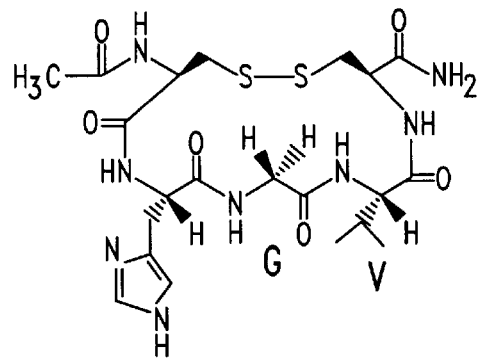
N-Ac-CHGVC-NH₂
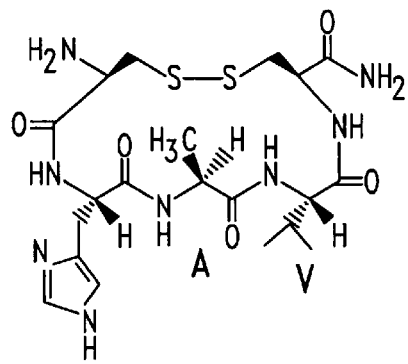
H-CHAVC-NH₂
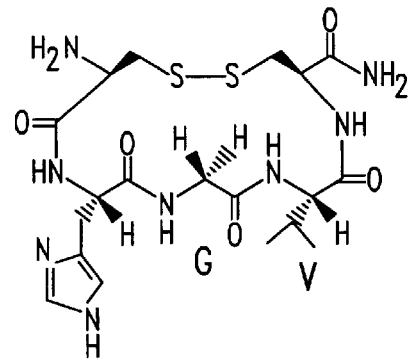
H-CHGVC-NH₂
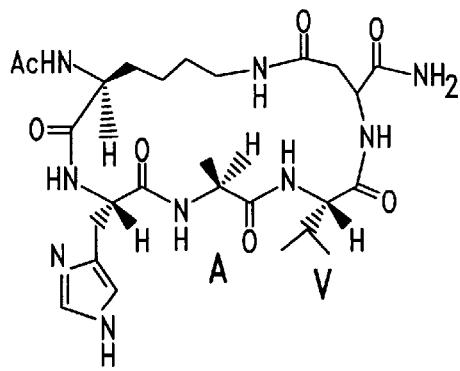
N-Ac-KHAVD-NH₂
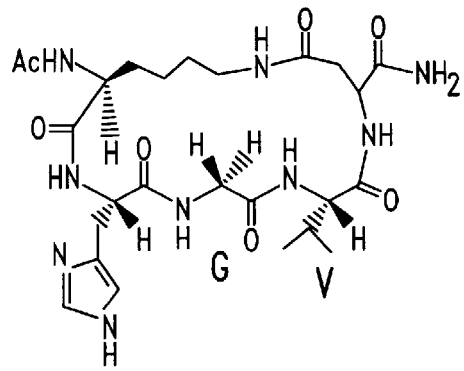
N-Ac-KHGVD-NH₂
Fig. 3A

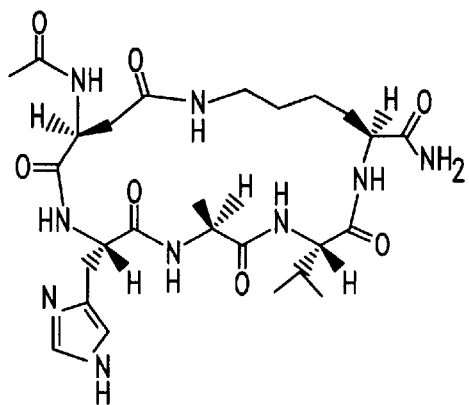
N-Ac-DHAVK-NH₂
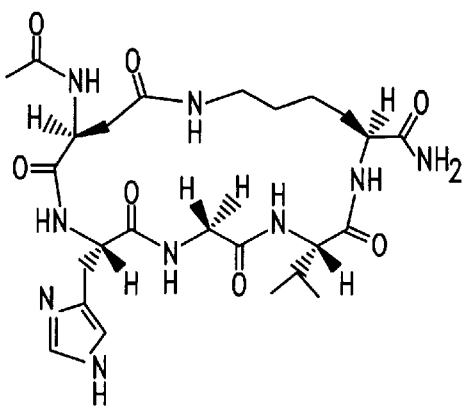
N-Ac-DHGVK-NH₂
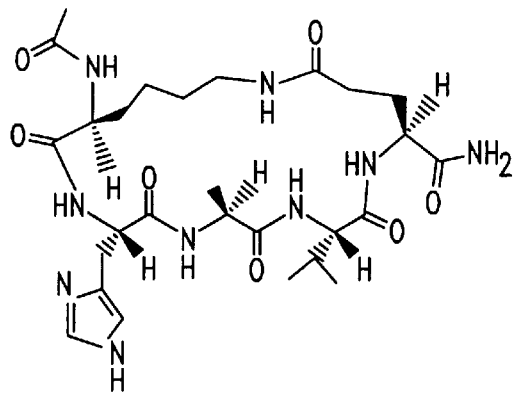
N-Ac-KHAVE-NH₂
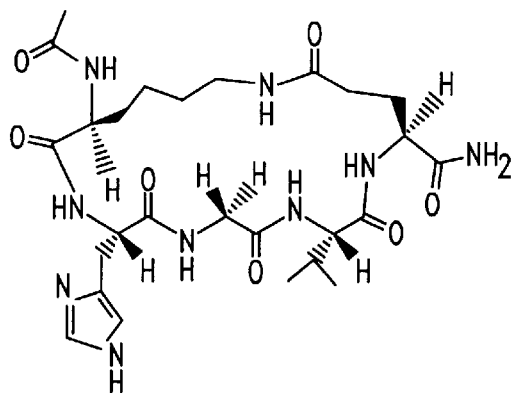
N-Ac-KHGVE-NH₂
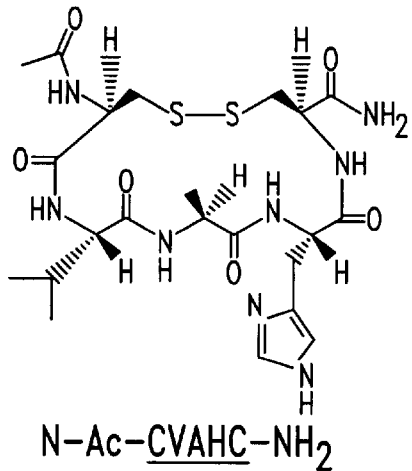
N-Ac-CVAHC-NH₂
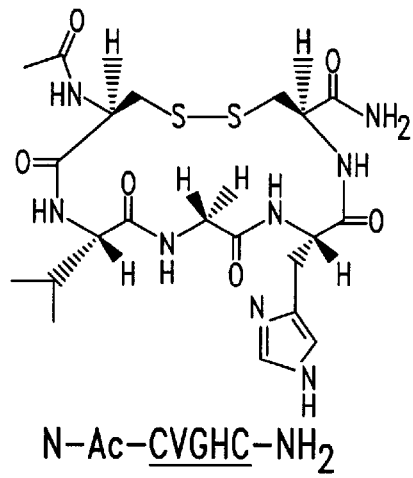
N-Ac-CVGHC-NH₂
*Fig. 3B*

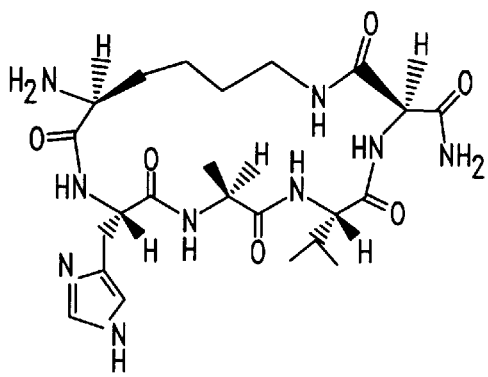
H-KHAVD-NH2
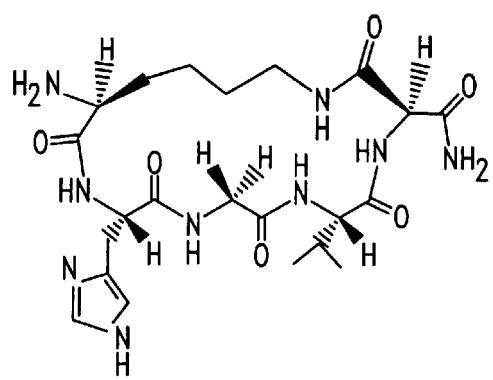
H-KHGVD-NH2
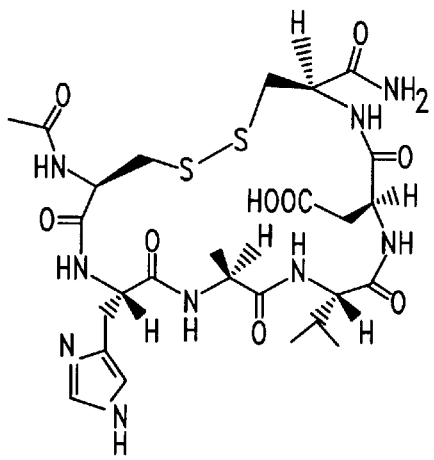
N-Ac-CHAVDC-NH2
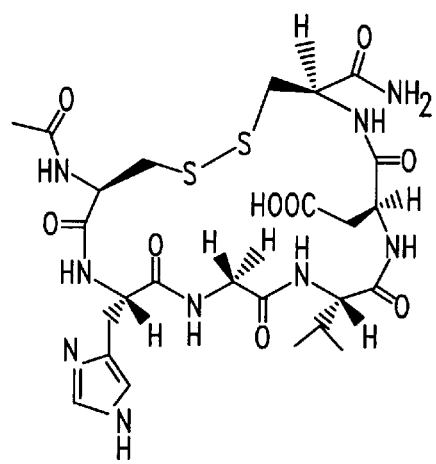
N-Ac-CHGVDC-NH2
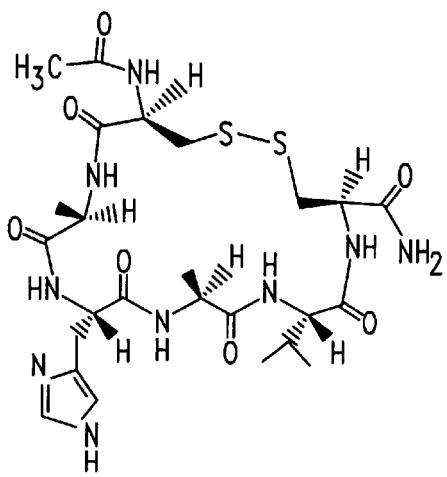
N-Ac-CAHAVC-NH2
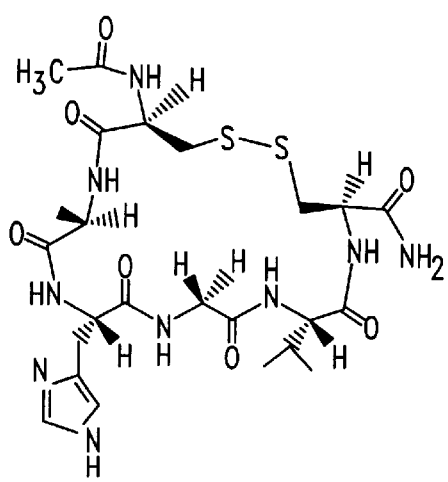
N-Ac-CAHGVC-NH2
Fig. 3C

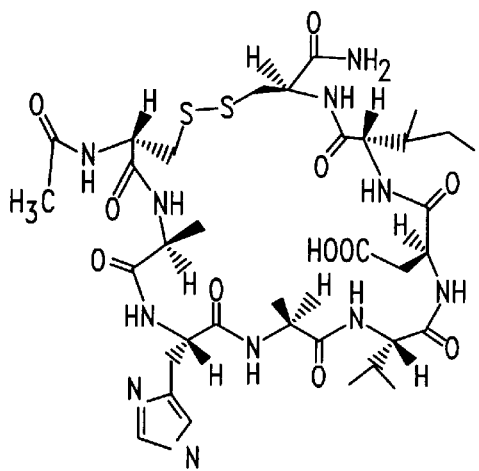
N-Ac-CAHAVDIC-NH₂
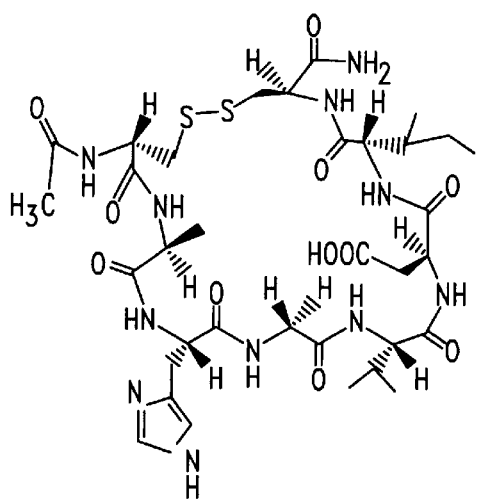
N-Ac-CAHGVDIC-NH₂
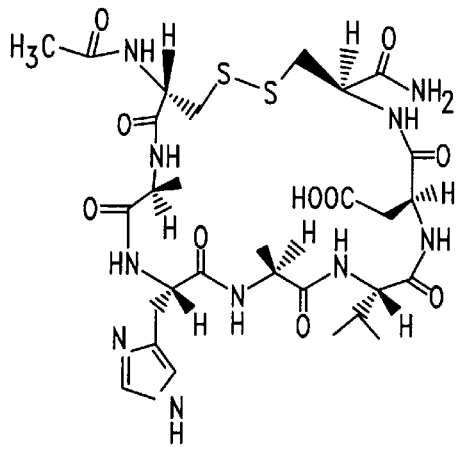
N-Ac-CAHAVDC-NH₂
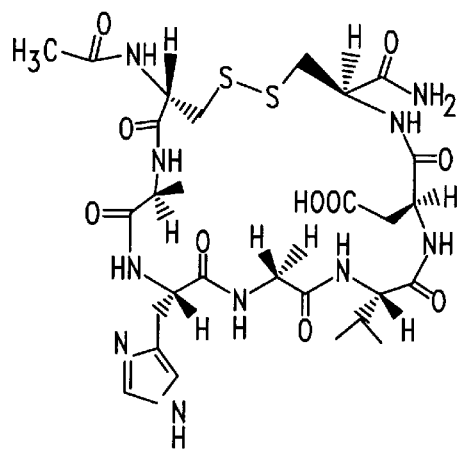
N-Ac-CAHGVDC-NH₂
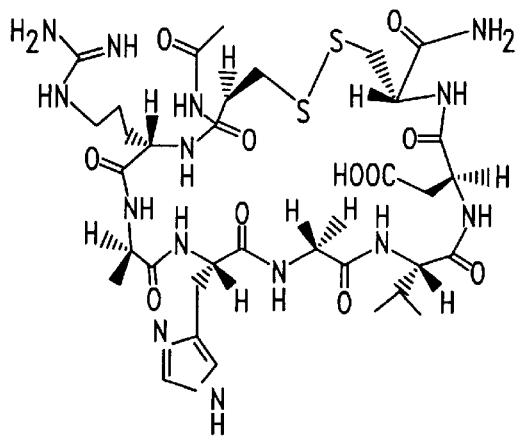
N-Ac-CRAHAVDC-NH₂
*Fig. 3D*
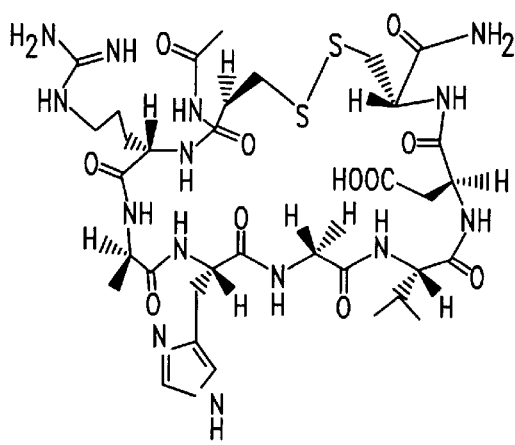
N-Ac-CRAHGVDC-NH₂

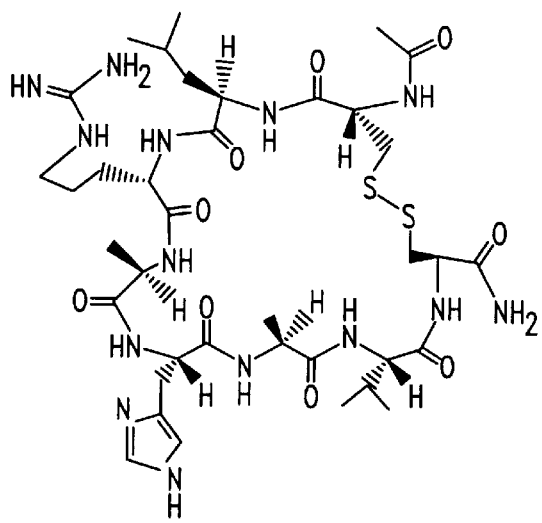
N-Ac-CLRAHAVC-NH₂
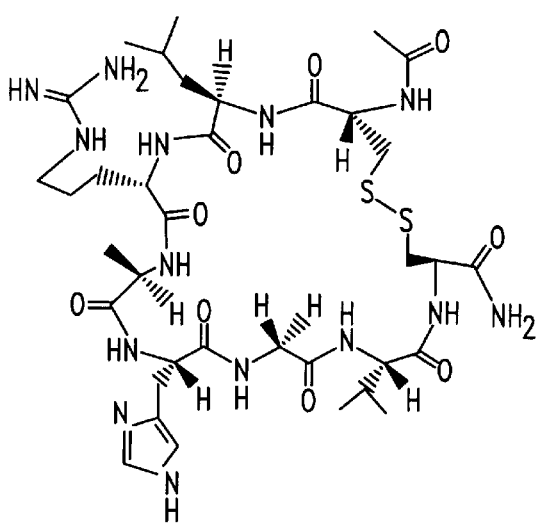
N-Ac-CLRAHGVC-NH₂
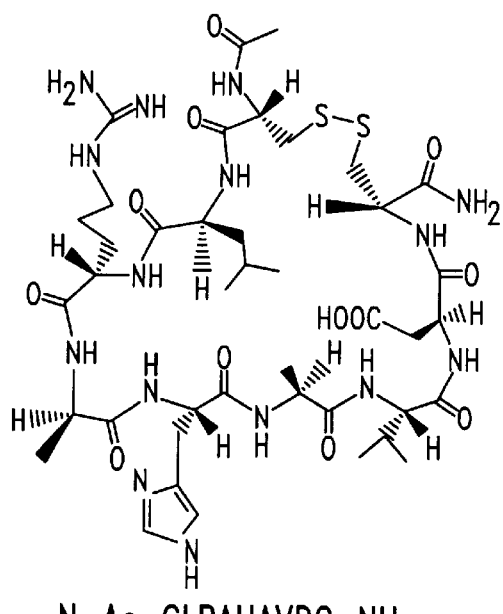
N-Ac-CLRAHAVDC-NH₂
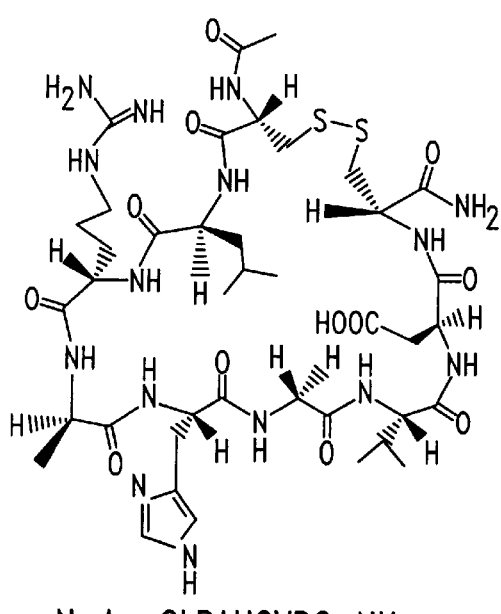
N-Ac-CLRAHGVDC-NH₂
*Fig. 3E*

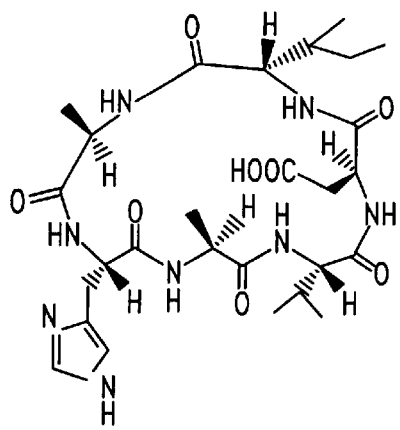
AHAVDI
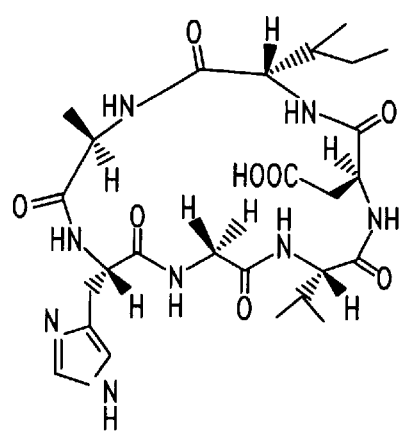
AHGVDI
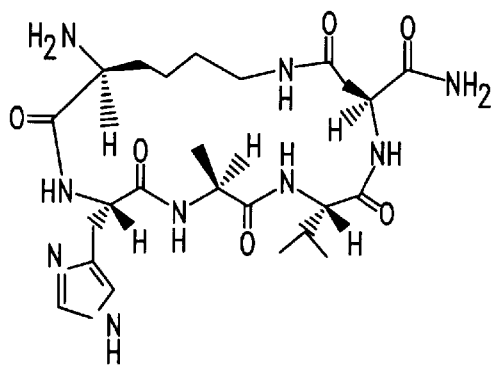
H-KHAVD-NH₂
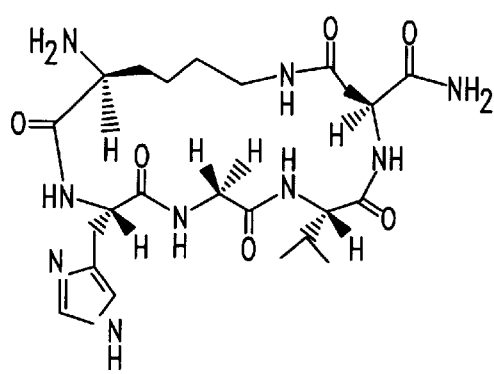
H-KHGVD-NH₂
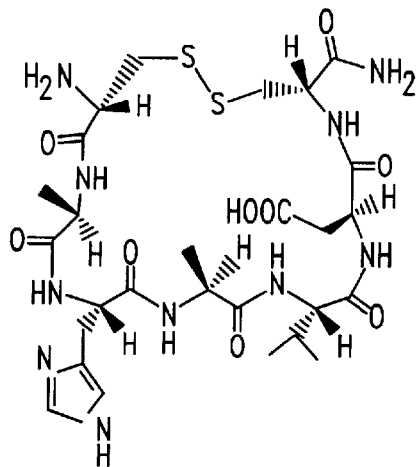
H-CAHAVDC-NH₂
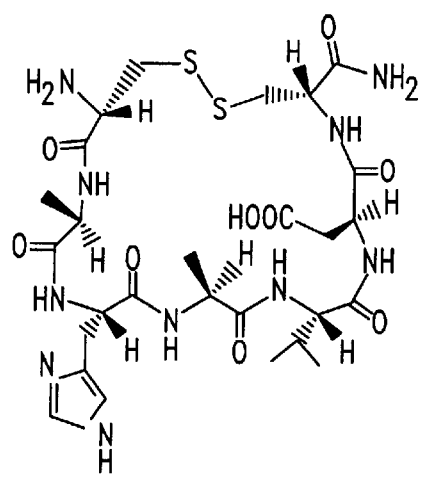
H-CAHGVDC-NH₂
*Fig. 3F*

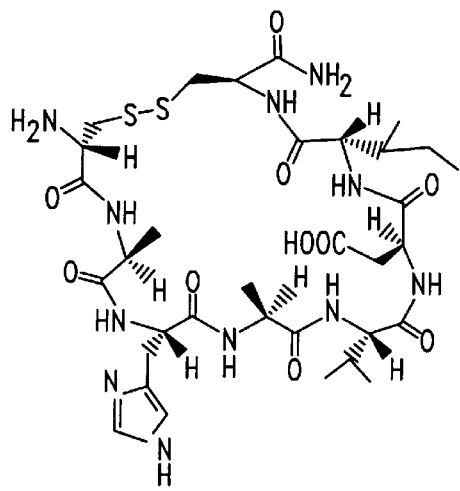
H-CAHAVDIC-NH₂
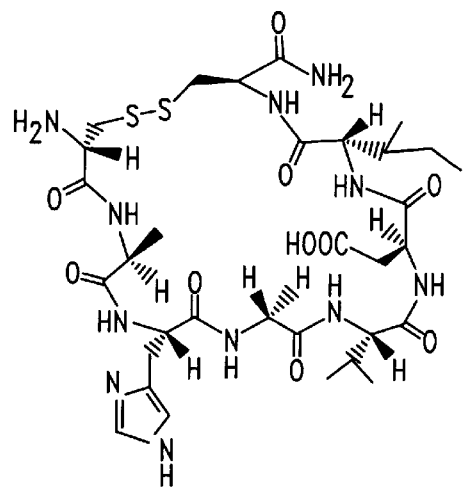
H-CAHGVDIC-NH₂
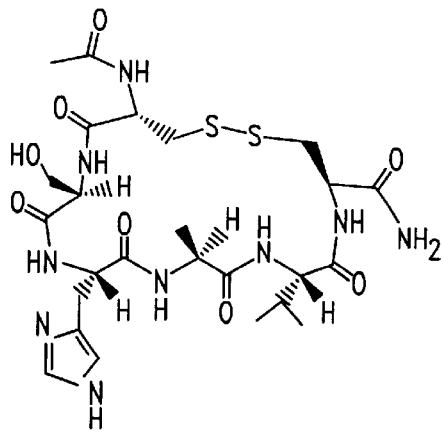
N-Ac-CSHAVC-NH₂
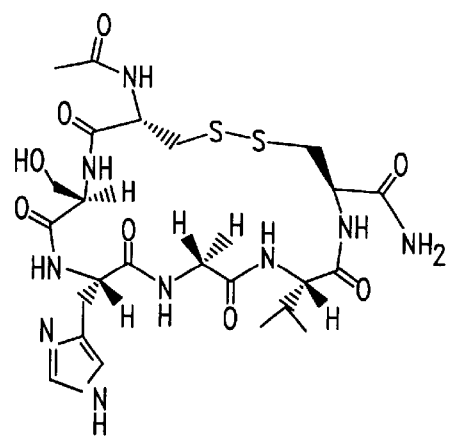
N-Ac-CSHGVC-NH₂
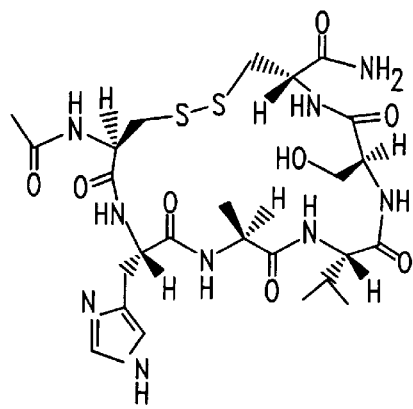
N-Ac-CHAVSC-NH₂
*Fig. 3G*
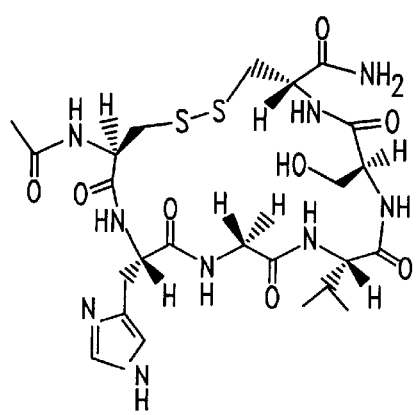
N-Ac-CHGVSC-NH₂

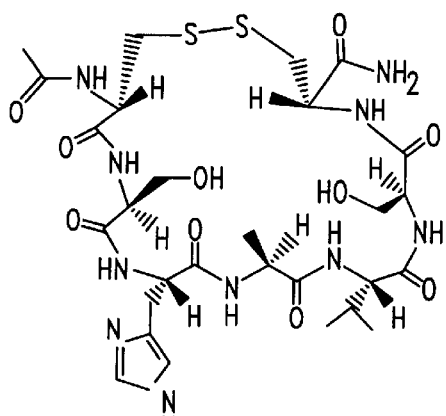
N-Ac-CSHAVSC-NH₂
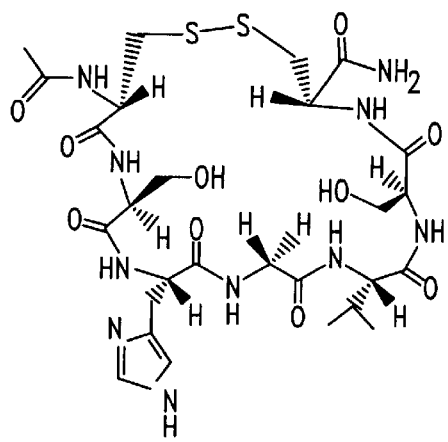
N-Ac-CSHGVSC-NH₂
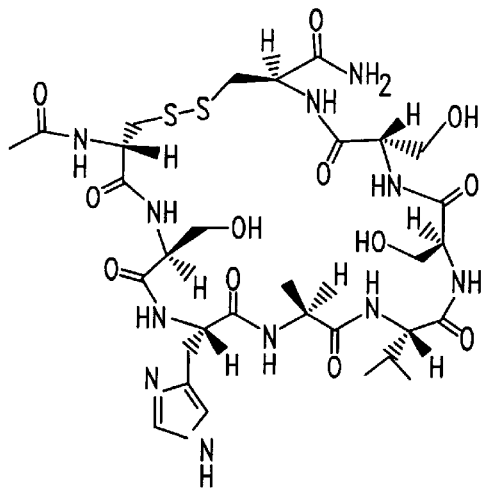
N-Ac-CSHAVSSC-NH₂
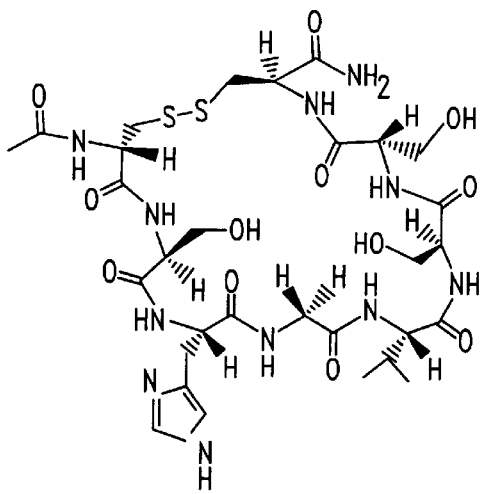
N-Ac-CSHGVSSC-NH₂
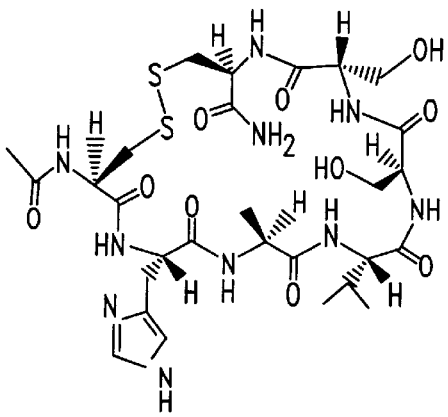
N-Ac-CHAVSSC-NH₂
*Fig. 3H*
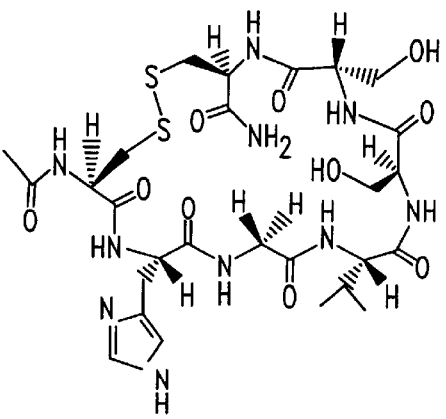
N-Ac-CHGVSSC-NH₂

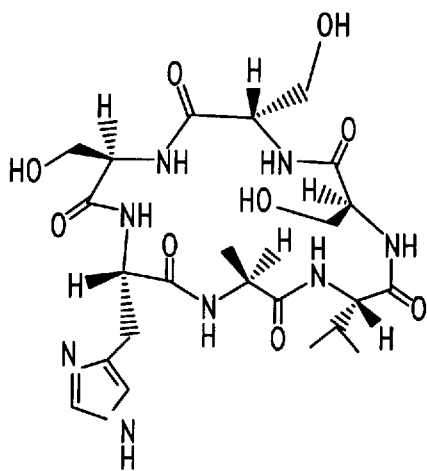
SHAVSS
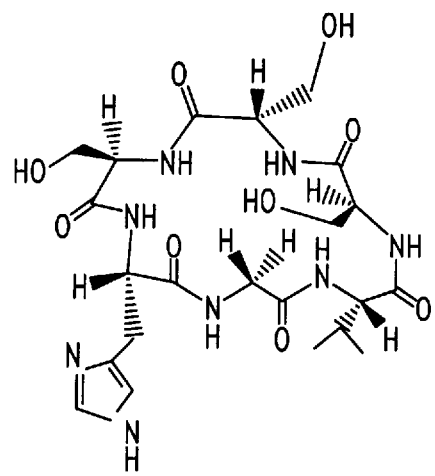
SHGVSS
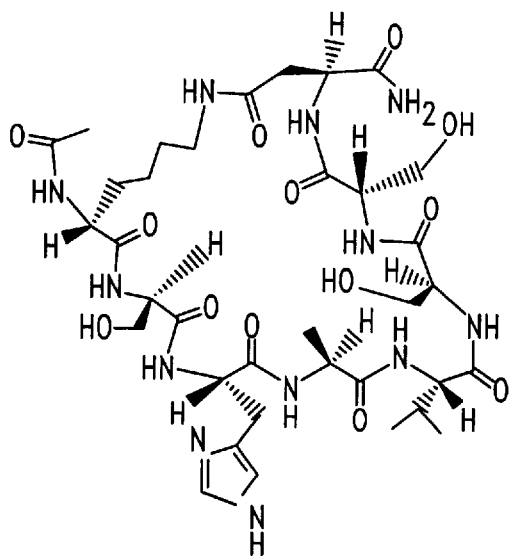
N-Ac-KSHAVSSD-NH$_2$
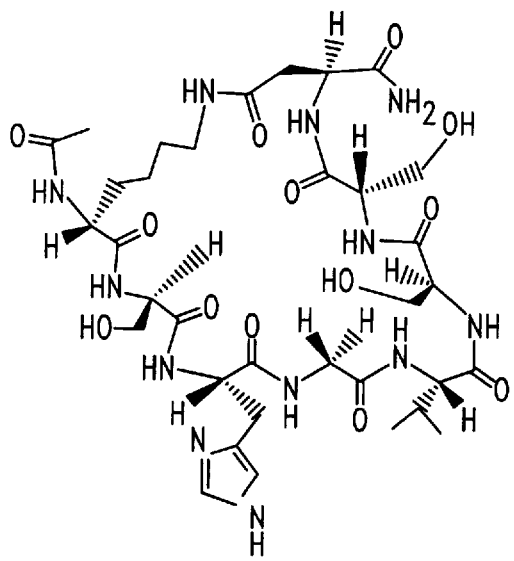
N-Ac-KSHGVSSD-NH$_2$
Fig. 3I

COMPOUNDS AND METHOD FOR MODULATING NEURITE OUTGROWTH

CROSS-REFERENCE TO RELATED APPLICATIONS

This application is a continuation-in-part of U.S. Ser. No. 09/115,395, filed Jul. 14, 1998, now pending which is a continuation-in-part of U.S. Ser. No. 08/996,679, filed Dec. 23, 1997, now U.S. Pat. No. 6,169,071 which is a continuation-in-part of U.S. Ser. No. 08/893,534, filed Jul. 11, 1997, now U.S. Pat. No. 6,031,072 which claims the benefit of U.S. Provisional Application No. 60/021,612, filed Jul. 12, 1996.

TECHNICAL FIELD

The present invention relates generally to methods for modulating N-cadherin mediated processes, and more particularly to the use of cyclic peptides comprising a cadherin cell adhesion recognition sequence for inhibiting or enhancing cadherin-mediated neurite outgrowth.

BACKGROUND OF THE INVENTION

Nerve growth is promoted by a wide range of molecules, including the cell surface adhesion molecules (CAMs) NCAM and N-cadherin. In particular, N-cadherin is the predominant mediator of calcium-dependent adhesion in the nervous system. N-cadherin is a member of the classical cadherin family of calcium-dependent CAMs (Munro et al., *In: Cell Adhesion and Invasion in Cancer Metastasis*, P. Brodt, ed., pp. 17–34, R G Landes Co.(Austin Tex., 1996). The classical cadherins (abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural)—cadherin is predominantly expressed by neural cells, endothelial cells and a variety of cancer cell types. A detailed discussion of the classical cadherins is provided in Munro SB et al., 1996, *In: Cell Adhesion and Invasion in Cancer Metastasis*, P. Brodt, ed., pp.17–34 (R G Landes Company, Austin Tex.).

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:8), DXD and LDRE (SEQ ID NO:9) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra, Blaschuk et al., *J. Mol. Biol.* 211:679–82, 1990; Blaschuk et al., *Develop. Biol.* 139:227–29, 1990; Alexander et al., *J. Cell. Physiol.* 156:610–18, 1993). The three-dimensional solution and crystal structures of the EC1 domain have been determined (Overduin et al., *Science* 267:386–389, 1995; Shapiro et al., *Nature* 374:327–337, 1995).

N-cadherin is known to promote neurite outgrowth via a homophilic binding mechanism. N-cadherin is normally found on both the advancing growth cone and on cellular substrates, and the inhibition of N-cadherin function results in diminished neurite outgrowth. Such inhibition may be the result of pathology or injury involving severed neuronal connections and/or spinal cord damage. In such cases, enhancement of N-cadherin mediated neurite outgrowth would be beneficial. However, previous attempts to promote neurite outgrowth have achieved limited success due, in part, to difficulties associated with maintaining continuous growth over a particular defined region.

Accordingly, there is a need in the art for compounds that modulate and/or direct neurite outgrowth without such disadvantages. The present invention fulfills this need and further provides other related advantages.

SUMMARY OF THE INVENTION

The present invention provides methods for modulating cadherin-mediated neurite outgrowth. Within one aspect, the present invention provides methods for enhancing and/or directing neurite outgrowth, comprising contacting a neuron with a cell adhesion modulating agent, wherein the modulating agent enhances cadherin-mediated cell adhesion.

Within a related aspect, methods for treating spinal cord injuries in a mammal are provided, comprising administering to a mammal a cell adhesion modulating agent as described above, wherein the modulating agent enhances cadherin-mediated cell adhesion.

Within the above aspects, cell adhesion modulating agents generally comprise a cyclic peptide in which nonadjacent amino acid residues are covalently linked to form a peptide ring, wherein the peptide ring comprises the sequence His-Ala-Val. Within certain embodiments, the cyclic peptide has the formula:

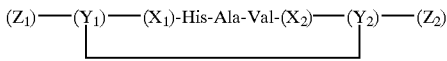

wherein $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and Y2 are independently selected from the group consisting of amino acid residues, and wherein a covalent bond is formed between residues $Y_1$ and Y2; and wherein $Z_1$ and $Z_2$ are optional, and if present, are independently selected from the group consisting of amino acid residues and combinations thereof in which the residues are linked by peptide bonds. Within certain specific embodiments $Z_1$ is not present and $Y_1$ comprises an N-acetyl group and/or $Z_2$ is not present and $Y_2$ comprises a C-terminal amide group. Linkage of $Y_1$ and Y2 may be achieved via, for example, a disulfide bond, an amide bond or a thioether bond.

Certain modulating agents comprise a cyclic peptide having the formula:

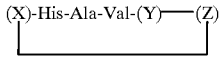

wherein Y is optional and, if present is selected from the group consisting of amino acid residues and combinations thereof in which the residues are linked by peptide bonds, and wherein Y ranges in size from 0 to 10 residues; and wherein X and Z are independently selected from the group consisting of amino acid residues, wherein a disulfide bond is formed between residues X and Z; and wherein X comprises an N-acetyl group.

Certain preferred modulating agents comprise a sequence selected from the group consisting of N-Ac-CHAVC-$NH_2$ (SEQ ID NO:10), N-Ac-CHAVDC-$NH_2$ (SEQ ID NO:20), N-Ac-CHAVDIC-$NH_2$ (SEQ ID NO:50), N-Ac-CHAVDINC-$NH_2$ (SEQ ID NO:51), N-Ac-CHAVDINGC-$NH_2$ (SEQ ID NO:76), N-Ac-CAHAVC-$NH_2$ (SEQ ID NO:22), N-Ac-CAHAVDC-$NH_2$ (SEQ ID NO:26), N-Ac-CAHAVDIC-$NH_2$ (SEQ ID NO:24), N-Ac-CRAHAVDC-$NH_2$ (SEQ ID NO:28), N-Ac-CLRAHAVDC-$NH_2$ (SEQ ID NO:32), N-Ac-DHAVK-$NH_2$ (SEQ ID NO:14), N-Ac-KHAVE-$NH_2$ (SEQ ID NO:16), N-Ac-AHAVDI-$NH_2$ (SEQ ID NO:34) and derivatives of the foregoing sequences having one or more C-terminal, N-terminal and/or side chain modifications.

Any of the above modulating agents may comprise multiple HAV sequences separated by a linker. Modulating agents may further be linked to one or more of a drug, a solid support, a targeting agent, a cell adhesion recognition sequence that is bound by an adhesion molecule other than a cadherin, wherein the cell adhesion recognition sequence is separated from any HAV sequence(s) by a linker; and/or an antibody or antigen-binding fragment thereof that specifically binds to a cell adhesion recognition sequence bound by an adhesion molecule other than a cadherin. A modulating agent may be present within a pharmaceutical composition that comprises a pharmaceutically acceptable carrier and, optionally, may further comprise a drug, a peptide comprising a cell adhesion recognition sequence that is bound by an adhesion molecule other than a cadherin; and/or an antibody or antigen-binding fragment thereof that specifically binds to a cell adhesion recognition sequence bound by an adhesion molecule other than a cadherin.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:8), DXD and LDRE (SEQ ID NO:9). The CAR sequence, HAV, is shown within EC1. Cytoplasmic proteins β-catenin (β), α-catenin (α) and (α-actinin (ACT), which mediate the interaction between CADs and microfilaments (MF) are also shown.

FIG. 2 provides the amino acid sequences of mammalian classical cadherin EC1 domains: human N-cadherin (SEQ ID NO:1), mouse N-cadherin (SEQ ID NO:2), cow N-cadherin (SEQ ID NO:3), human P-cadherin (SEQ ID NO:4), mouse P-cadherin (SEQ ID NO:5), human E-cadherin (SEQ ID NO:6) and mouse E-cadherin (SEQ ID NO:7).

FIGS. 3A–3I provide the structures of representative cyclic peptides of the present invention (SEQ ID NOs: 10, 12, 14, 16, 18, 20, 22, 24, 26, 28, 30, 32, 34, 36, 38, 40, 42, 44, 46 and 48; structures on the left hand side), along with similar, but inactive, structures (SEQ ID NOs: 11, 13, 15, 17, 19, 21, 23, 25, 27, 29, 31, 33, 35, 37, 39, 41, 43, 45, 47 and 49; on the right).

FIG. 4 is a histogram depicting the mean neurite length in microns for neurons grown in the presence (solid bars) or absence (cross-hatched bars) of 500 μg/mL of the representative cyclic peptide N-Ac-CHAVC-$NH_2$ (SEQ ID NO:10).

In the first pair of bars, neurons were grown on a monolayer of untransfected 3T3 cells. In the remaining columns, the mean neurite length is shown for neurons cultured on 3T3 cells transfected with cDNA encoding N-CAM (second pair of bars), L1 (third pair of bars) or N-cadherin (fourth pair of bars).

FIG. 5 is a histogram illustrating the ability of various representative modulating agents to inhibit neurite outgrowth. The percent inhibition is shown for the cyclic peptide modulating agents indicated.

FIG. 6 is a graph illustrating the results of a study to assess the chronic toxicity of a representative cyclic peptide. The graph presents the mean body weight during the three-day treatment period (one intraperitoneal injection per day) and the four subsequent recovery days. Three different doses are illustrated, as indicated.

FIG. 7 is a graph illustrating the stability of a representative cyclic peptide in mouse whole blood. The percent of the cyclic peptide remaining in the blood was assayed at various time points, as indicated.

FIG. 8 is a bar graph showing the effect of N-Ac-CHAVC-$NH_2$ (SEQ ID NO:10) and N-Ac-CHGVC-$NH_2$ (SEQ ID NO:11) on N-cadherin-mediated neurite outgrowth. Mean neurite length is shown for cerebellar neurons cultured for 14 hours on monolayers of control 3T3 cells (unshaded), on N-cadherin expressing 3T3 cells (diagonal rising right), on N-cadherin expressing 3T3 cells in media supplemented with N-Ac-CHAVC-$NH_2$ (SEQ ID NO:10; diagonal cross hatch) and on N-cadherin expressing 3T3 cells in media supplemented with N-Ac-CHGVC-$NH_2$ (SEQ ID NO:11; diagonal rising left). The results show the mean length of the longest neurite measured in a single representative experiment, and the error bars show the s.e.m.

FIG. 9 is a graph showing dose-response curves that illustrate the inhibition of neurite outgrowth over both 3T3 cells and N-cadherin expressing 3T3 cells in the presence of increasing concentrations of N-Ac-CHAVC-$NH_2$ (SEQ ID NO:10). The peptide had no effect on the basal growth over 3T3 cells. The $EC_{50}$ value was determined to be 0.22 mM.

FIG. 10 is a bar graph illustrating the effects of the cyclic peptides N-Ac-CHAVDC-$NH_2$ (SEQ ID NO:20), N-Ac-CHAVDIC-$NH_2$ (SEQ ID NO:50) and N-Ac-CHAVDINC-$NH_2$ (SEQ ID NO:51) on L1 function. Cerebellar neurons were cultured on monolayers of control 3T3 cells and L1 expressing 3T3 cells for 16–18 hours in control media (unshaded) or control media supplemented with peptides N-Ac-CHAVDC-$NH_2$ (SEQ ID NO:20; diagonal rising right), N-Ac-CHAVDIC-$NH_2$ (SEQ ID NO:50; diagonal cross hatch) or N-Ac-CHAVDINC-$NH_2$ (SEQ ID NO:51; diagonal rising left) at a concentration of 100 μg/mL. The cultures were then fixed and neurite outgrowth determined by measuring the length of the longest neurite from a total of 150–200 neurons sampled in replicate cultures for each experimental condition. The results show $L_1$ response, measured as a percentage increase in the mean length of the longest neurite relative to the 3T3 control value, for neurons grown in the absence or presence of the test peptide. The results are pooled from three independent experiments, and the bars show the s.e.m.

FIG. 11 is a graph dose-response curve that illustrates the inhibition of neurite outgrowth over N-cadherin expressing 3T3 cells in the presence of increasing concentrations of N-Ac-CHAVDC-$NH_2$ (SEQ ID NO:20).

FIG. 12 is a graph dose-response curve that illustrates the inhibition of neurite outgrowth over N-cadherin expressing 3T3 cells in the presence of increasing concentrations of N-Ac-CHAVDIC-$NH_2$ (SEQ ID NO:50).

FIG. 13 is a graph dose-response curve that illustrates the inhibition of neurite outgrowth over N-cadherin expressing 3T3 cells in the presence of increasing concentrations of N-Ac-CHAVDINC-NH₂ (SEQ ID NO:5 1).

DETAILED DESCRIPTION OF THE INVENTION

As noted above, the present invention provides cell adhesion modulating agents that are capable of modulating cadherin-mediated processes, such as neurite outgrowth. In general, to modulate (i.e., enhance, inhibit and/or direct) neurite outgrowth, a cadherin-expressing neuron is contacted with a cell adhesion modulating agent (also referred to herein as a "modulating agent") either in vivo or in vitro. A modulating agent generally comprises a cyclic peptide that contains the classical cadherin cell adhesion recognition (CAR) sequence HAV (i.e., His-Ala-Val). Such modulating agents may further comprise one or more additional CAR sequences and/or an antibody (or antigen-binding fragment thereof) that specifically binds to a cadherin or other CAR sequence, as described below.

Cell Adhesion Modulating Agents

The term "cell adhesion modulating agent," as used herein, refers to a molecule comprising at least one cyclic peptide that contains a cadherin cell adhesion recognition (CAR) sequence, generally HAV (His-Ala-Val). The term "cyclic peptide," as used herein, refers to a peptide or salt thereof that comprises (1) an intramolecular covalent bond between two non-adjacent residues, forming a cyclic peptide ring and (2) at least one cadherin CAR sequence located within the ring. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. In addition to the cadherin CAR sequence HAV, a modulating agent may comprise additional CAR sequences, which may or may not be cadherin CAR sequences, and/or antibodies or fragments thereof that specifically recognize a CAR sequence. Additional CAR sequences may be present within the cyclic peptide containing the HAV sequence, within a separate cyclic peptide component of the modulating agent and/or in a non-cyclic portion of the modulating agent. Antibodies and antigen-binding fragments thereof are typically present in a non-cyclic portion of the modulating agent.

In addition to the CAR sequence(s), cyclic peptides generally comprise at least one additional residue, such that the size of the cyclic peptide ring ranges from 4 to about 15 residues, preferably from 5 to 10 residues. Such additional residue(s) may be present on the N-terminal and/or C-terminal side of a CAR sequence, and may be derived from sequences that flank the HAV sequence within one or more naturally occurring cadherins (e.g., N-cadherin) with or without amino acid substitutions and/or other modifications. Flanking sequences for endogenous N-, E-, P- and R-cadherin are shown in FIG. 2, and in SEQ ID NOs: 1 to 7. For modulating neurite outgrowth, such flanking sequences are preferably derived from N-cadherin. Database accession numbers for representative naturally occurring N-cadherins are as follows: human N-cadherin M34064, mouse N-cadherin M31131 and M22556 and cow N-cadherin X53615. Alternatively, additional residues present on one or both sides of the CAR sequence(s) may be unrelated to an endogenous sequence (e.g., residues that facilitate cyclization).

Within certain preferred embodiments, as discussed below, relatively small cyclic peptides that do not contain significant sequences flanking the HAV sequence are preferred. Such peptides may contain an N-acetyl group and a C-amide group (e.g., the 5-residue ring N-Ac-CHAVC-NH₂ (SEQ ID NO:10)). Such cyclic peptides can be thought of as "master keys" that fit into peptide binding sites of each of the different classical cadherins, and are capable of modulating neurite outgrowth as well as adhesion of neural cells, endothelial cells, epithelial cells and/or certain cancer cells. Small cyclic peptides may generally be used to specifically modulate neurite outgrowth by topical administration or by systemic administration, with or without linking a targeting agent to the peptide, as discussed below.

Within other preferred embodiments, as noted above, a cyclic peptide may contain sequences that flank the HAV sequence on one or both sides that are designed to confer specificity for a function of one or more specific cadherins (e.g., N-cadherin), resulting in tissue and/or cell-type specificity. Suitable flanking sequences for conferring specificity include, but are not limited to, endogenous sequences present in one or more naturally occurring cadherins, and cyclic peptides having specificity may be identified using the representative screens provided herein. For example, it has been found, within the context of the present invention, that cyclic peptides that contain additional residues derived from the native N-cadherin sequence disrupt N-cadherin mediated interactions with a high degree of specificity (i.e., such peptides do not significantly disrupt E-cadherin mediated interactions). Within preferred embodiments, such a cyclic peptide comprises at least one residue derived from a native N-cadherin sequence on the C-terminal side of the HAV sequence.

To facilitate the preparation of cyclic peptides having a desired specificity, nuclear magnetic resonance (NMR) and computational techniques may be used to determine the conformation of a peptide that confers a known specificity. NMR is widely used for structural analysis of both peptidyl and non-peptidyl compounds. Nuclear Overhauser Enhancements (NOE's), coupling constants and chemical shifts depend on the conformation of a compound. NOE data provide the distance between protons through space and across the ring of the cyclic peptide, and can be used to calculate the lowest energy conformation for the CAR sequence. Cyclic peptides are conformationally restricted and exist in the active conformation a much higher percentage of the time than to the corresponding linear peptides. Linear peptides in solution exist in many conformations. Using a cyclic peptide, it is possible to fix the peptide in the active conformation. Conformation may then be correlated with tissue specificity to permit the identification of peptides that are similarly tissue specific or have enhanced tissue specificity.

As noted above, multiple CAR sequences may be present within a modulating agent. In some cases, multiple HAV sequences may be present, preferably separated by a linker as described below. Other CAR sequences may also, or alternatively, be included within a modulating agent. In general, a modulating agent may comprise any sequence specifically bound by an adhesion molecule. As used herein, an "adhesion molecule" is any molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins, such as OB-cadherin), as well as integrins and members of the immunoglobulin supergene family, such as N-CAM Preferred CAR sequences for inclusion within a modulating agent include Arg-Gly-Asp (RGD), which is bound by integrins (see Cardarelli et al., *J. Biol. Chem.* 267:23159–64, 1992); Tyr-Ile-Gly-Ser-Arg (YIGSR; SEQ ID NO:52), which is bound by (α6β1 integrin; KYSFNYDGSE (SEQ ID NO:53), which is bound by N-CAM; and the N-CAM heparin sulfate-binding site IWKHKGRDVILKKDVRF (SEQ ID NO:54). Other preferred CAR sequences are nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO:57), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative nonclassical cadherin CAR sequences include the cadherin-7 CAR sequences DEN, EPK and DAN; the cadherin-8 CAR sequences EEF and NDV; the OB-cadherin (cadherin-11) CAR sequences DDK, EEY and EAQ; the cadherin-12 CAR sequences DET and DPK; the cadherin-14 CAR sequences DDT, DPK and DAN; the cadherin-15 CAR sequences DKF and DEL; the PB-cadherin CAR sequences EEY, DEL, DPK and DAD; the protocadherin CAR sequences DLV, NRD, DPK and DPS; and the cadherin-related neuronal receptor CAR sequences DPV, DAD, DSV, DSN, DSS, DEK and NEK. A variety of peptides comprising an OB-cadherin CAR sequence may be included, such as IDDK (SEQ ID NO:55), DDKS (SEQ ID NO:56), VIDDK (SEQ ID NO:58), IDDKS (SEQ ID NO:59), VIDDKS (SEQ ID NO:60), DDKSG (SEQ ID NO:61), IDDKSG (SEQ ID NO:77), VIDDKSG (SEQ ID NO:78), FVIDDK (SEQ ID NO:82), FVIDDKS (SEQ ID NO:83), FVIDDKSG (SEQ ID NO:84), IFVIDDK (SEQ ID NO:85), IFVIDDKS (SEQ ID NO:86), or IFVIDKSG (SEQ ID NO:87).

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Using a linker, HAV-containing cyclic peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO:52) and HAV, one or more of which are present within a cyclic peptide. Within another embodiment, modulating agents having a branched structure comprise RGD, YIGSR (SEQ ID NO:52), HAV and KYSFNYDGSE (SEQ ID NO:53). Bi-functional modulating agents that comprise an HAV sequence with flanking E-cadherin-specific sequences joined via a linker to an HAV sequence with flanking N-cadherin-specific sequences are also preferred for certain embodiments.

Linkers preferably produce a distance between CAR sequences between 0.1 to 10,000 nm, more preferably about 0.1–400 nm. A separation distance between recognition sites may generally be determined according to the desired function of the modulating agent. For inhibitors of neurite outgrowth, the linker distance should be small (0.1–400 nm). For enhancers of neurite outgrowth, the linker distance should be 400–10,000 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and omithine 2.44 or 5.61 angstroms. Peptide and non-peptide linkers may generally be incorporated into a modulating agent using any appropriate method known in the art.

Modulating agents that inhibit neurite outgrowth typically contain one HAV sequence or multiple HAV sequences, which may be adjacent to one another (i.e., without intervening sequences) or in close proximity (i.e., separated by peptide and/or non-peptide linkers to give a distance between the CAR sequences that ranges from about 0.1 to 400 nm). Within one such embodiment, the cyclic peptide contains two HAV sequences. Such a modulating agent may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the HAV sequence(s) and/or each other. Such modulating agents may generally be used within methods in which it is desirable to simultaneously disrupt cell adhesion mediated by multiple adhesion molecules. Within certain preferred embodiments, the second CAR sequence is derived from fibronectin and is recognized by an integrin (i.e., RGD; see Cardarelli et al., *J. Biol. Chem.* 267:23159–23164, 1992). Other preferred CAR sequences include YIGSR (SEQ ID NO:52) and KYSFNYDGSE (SEQ ID NO:53). One or more antibodies, or fragments thereof, may similarly be used within such embodiments.

Modulating agents that enhance neurite outgrowth may contain multiple HAV sequences, and/or antibodies that specifically bind to such sequences, joined by linkers as described above. Enhancement of cell adhesion may also be achieved by attachment of multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

Modulating agents and cyclic peptides as described herein may comprise residues of L-amino acids, D-amino acids, or any combination thereof. Amino acids may be from natural or non-natural sources, provided that at least one amino group and at least one carboxyl group are present in the molecule; a- and P-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Modulating agents and cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, omithine, diaminobutyric acid, α-aminoadipic acid, m-aminomethylbenzoic acid and α,β-diaminopropionic acid.

TABLE 1

Amino acid one-letter and three-letter abbreviations

| | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Modulating agents and cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc. 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing H₂O as a side product. Alternatively, strong oxidizing agents such as I₂ and K₃Fe(CN)₆ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs: 62 and 63), in which the underlined portion is cyclized:

FmocCysAsp(t-Bu)GlyTyr(t-Bu)ProLys(Boc)Asp(t-Bu)CysLys(t-Bu)Gly-OMe
→

Fmoc CysAsp(t-Bu)GlyTyr(t-Bu)ProLys(Boc)Asp(t-Bu)CysLys(t-Bu)Gly-OMe

Oxidizing agents also allow concurrent deprotection/oxidation of suitable S-protected linear precursors to avoid premature, nonspecific oxidation of free cysteine, as shown below (SEQ ID NOs: 64 and 65), where X and Y=S-Trt or S-Acm:

BocCys(X)GlyAsnLeuSer(t-Bu)Thr(t-Bu)Cys(Y)MetLeuGlyOH→
Boc CysGlyAsnLeuSer(t-Bu)Thr(t-Bu)CysMetLeuGlyOH

DMSO, unlike I₂ and K₃Fe(CN)₆, is a mild oxidizing agent which does not cause oxidative side reactions of the nucleophilic amino acids mentioned above. DMSO is miscible with H₂O at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs: 66 and 67), X is Acm, Tacm or t-Bu:

H-Cys(X)TyrIleGlnAsnCys(X)ProLeuGly-NH₂→
H-CysTyrIleGlnAsnCysProLeuGly-NH₂

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by —NH₂:

i) N-Ac-Cys-His-Ala-Val-Cys-NH₂ (SEQ ID NO:10)
ii) N-Ac-Cys-Ala-His-Ala-Val-Asp-Ile-Cys-NH₂ (SEQ ID NO:24)
iii) N-Ac-Cys-Ser-His-Ala-Val-Cys-NH₂ (SEQ ID NO:36)
iv) N-Ac-Cys-His-Ala-Val-Ser-Cys-NH₂ (SEQ ID NO:38)
v) N-Ac-Cys-Ala-His-Ala-Val-Asp-Cys-NH₂ (SEQ ID NO:26)
vi) N-Ac-Cys-Ser-His-Ala-Val-Ser-Ser-Cys-NH₂ (SEQ ID NO:42)
vii) N-Ac-Cys-His-Ala-Val-Ser-Cys-OH (SEQ ID NO:38)
viii) H-Cys-Ala-His-Ala-Val-Asp-Cys-NH₂ (SEQ ID NO:26)
ix) N-Ac-Cys-His-Ala-Val-Pen-NH₂ (SEQ ID NO:68)
x) N-Ac-Ile-Tmc-Tyr-Ser-His-Ala-Val-Ser-Cys-Glu-NH₂ (SEQ ID NO:69)
xi) N-Ac-Ile-Pmc-Tyr-Ser-His-Ala-Val-Ser-Cys-NH₂ (SEQ ID NO:70)
xii) Mpr-Tyr-Ser-His-Ala-Val-Ser-Ser-Cys-NH₂ (SEQ ID NO:71)
xiii) Pmp-Tyr-Ser-His-Ala-Val-Ser-Ser-Cys-NH₂ (SEQ ID NO:72)

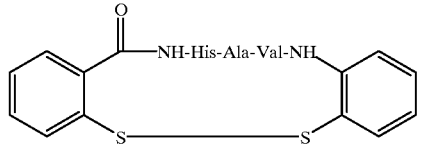

xii)

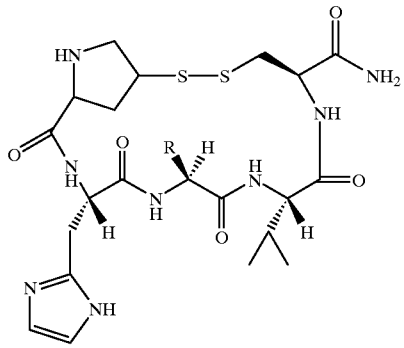

xiii)

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are AHAVDI (SEQ ID NO:34) and SHAVSS (SEQ ID NO:46), with or without an N-terminal acetyl group and/or a C-terminal amide. Within another such embodiment, the linear peptide comprises a D-amino acid (e.g., HAVsS; SEQ ID NO:73). Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

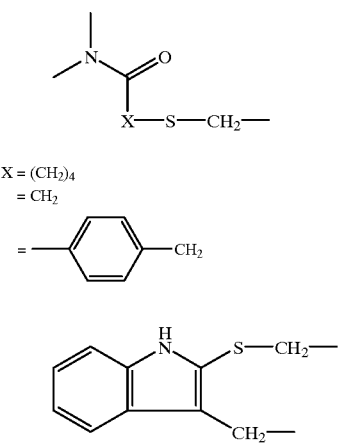

Cyclization may also be achieved using $\delta_1,\delta_{1'}$-Ditryptophan (i.e., Ac-<u>Trp-Gly-Gly-Trp</u>-OMe) (SEQ ID NO:74), as shown below:

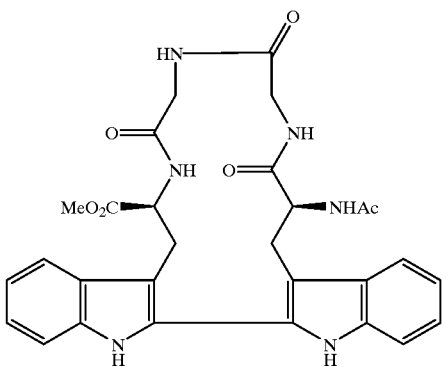

Representative structures of cyclic peptides are provided in FIG. 3. Within FIG. 3, certain cyclic peptides having the ability to modulate cell adhesion (shown on the left) are paired with similar inactive structures (on the right). The structures and formulas recited herein are provided solely for the purpose of illustration, and are not intended to limit the scope of the cyclic peptides described herein.

As noted above, a modulating agent may consist entirely of one or more cyclic peptides, or may contain additional peptide and/or non-peptide sequences, which may be linked to the cyclic peptide(s) using conventional techniques. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679–682, 1990), or from sequences isolated by screening an appropriate library with probes designed based on the sequences of known cadherins. Such screens may generally be performed as described in Sambrook et al., *Molecular Cloning: A Laboratory Manual,* Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a peptide portion of a modulating agent, an endogenous sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding a portion of the modulating agent.

As noted above, portions of a modulating agent may comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., *Develop. Dynamics* 197:1–13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a CAR sequence is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the cyclic peptide of interest may be prepared, for example, using the technique of Kohler and Milstein, *Eur. J. Immunol* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the polypeptide. Hybridomas having high reactivity and specificity are preferred. Monoclonal antibodies may be specific for particular cadherins (e.g., antibodies may bind to N-cadherin, without binding significantly to E-cadherin).

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular cadherins (e.g., the antibodies bind to N-cadherin, but do not bind significantly to E-cadherin). Such antibodies may be prepared as described above, using an immunogen that comprises (in addition to the HAV sequence) sufficient flanking sequence to generate the desired specificity (e.g., 5 amino acids on each side is generally sufficient). One representative immunogen is the 15-mer FHLRAHAVDINGNQV-NH$_2$ (SEQ ID NO:75), linked to KLH (see Newton et al., *Dev. Dynamics* 197:1–13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

The use of antigen-binding fragments of antibodies may be preferred within certain embodiments. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, cyclic peptides and other modulating agents as described herein are capable of modulating (i.e., enhancing, inhibiting and/or directing) cadherin-mediated neurite outgrowth. Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49–55, 1994; Williams et al., *Neuron* 13:583–594, 1994; Hall et al., *Cell Adhesion and Commun.* 3:441–450, 1996; Doherty and Walsh, *Mol. Cell. Neurosci.* 8:99–111, 1994; and Safell et al., *Neuron* 18:231–242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2%FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 μg/mL of a modulating agent that disrupts neural cell adhesion should result in a decrease in the mean neurite length by at least 50%, relative to the length in the absence of modulating agent or in the presence of a negative control peptide. Alternatively, the presence of 500 μg/mL of a modulating agent that enhances neural cell adhesion should result in an increase in the mean neurite length by at least 50%.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an RGD sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multifunctional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., OB-cadherin); integrins; members of the immunoglobulin supergene family, such as N-CAM; and other uncategorized transmembrane proteins. Preferred CAR sequences for use within such a modulator include RGD, YIGSR (SEQ ID NO:52), KYSFNYDGSE (SEQ ID NO:53), IWKH-KGRDVILKKDVRF (SEQ ID NO:54), the cadherin-7 CAR sequences DEN, EPK and DAN; the cadherin-8 CAR sequences EEF and NDV; the OB-cadherin (cadherin-11) CAR sequences DDK, EEY and EAQ; the cadherin-12 CAR sequences DET and DPK; the cadherin-14 CAR sequences DDT, DPK and DAN; the cadherin-15 CAR sequences DKF and DEL; the PB-cadherin CAR sequences EEY, DEL, DPK and DAD; the protocadherin CAR sequences DLV, NRD, DPK and DPS; and the cadherin-related neuronal receptor CAR sequences DPV, DAD, DSV, DSN, DSS, DEK and NEK.

A pharmaceutical composition may also contain one or more drugs, which may be linked to a modulating agent or may be free within the composition. Virtually any drug may be administered in combination with a cyclic peptide as described herein, for a variety of purposes.

The compositions described herein may be administered as part of a sustained release formulation (i.e., a formulation such as a capsule or sponge that effects a slow release of cyclic peptide following administration). Such formulations may generally be prepared using well known technology and administered by, for example, oral, rectal or subcutaneous implantation, or by implantation at the desired target site. Sustained-release formulations may contain a cyclic peptide dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of cyclic peptide release. The amount of cyclic peptide contained within a sustained release formulation depends upon the site of implantation, the rate and expected duration of release and the nature of the condition to be treated or prevented.

Pharmaceutical compositions of the present invention may be administered in a manner appropriate to the condition to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 μg to 2 mg/mL cyclic peptide. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating neurite outgrowth of cadherin-expressing neural cells in vitro and/or in vivo. As noted above, modulating agents for purposes that involve the disruption of cadherin-mediated neurite outgrowth may comprise a cyclic peptide containing a single HAV sequence, multiple HAV sequences in close proximity and/or an antibody (or an antigen-binding fragment thereof) that recognizes a cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the HAV sequence by linkers. As noted above, such linkers may or may not comprise one or more amino acids. For enhancing neurite outgrowth, a modulating agent may contain multiple HAV sequences or antibodies (or fragments), preferably separated by linkers, and/or may be linked to a single molecule or to a support material as described above. Within the methods described herein, one or more modulating agents may generally be administered alone, or within a pharmaceutical composition. In each specific method described herein, as noted above, a targeting agent may be employed to increase the local concentration of modulating agent at the target site.

Modulating agents may generally be used, within certain aspects, to enhance and/or direct neurological growth. In one aspect, neurite outgrowth may be enhanced and/or directed by contacting a neuron with one or more modulating agents. Preferred modulating agents for use within such methods are linked to a polymeric matrix or other support and include those peptides without substantial flanking sequences, as described above. In particularly preferred embodiments, the modulating agent comprises a cyclic peptide such as CHAVC (SEQ ID NO:10), CHAVDC (SEQ ID NO:11), CHAVDIC (SEQ ID NO:50), CHAVDINC (SEQ ID NO:51), CHAVDINGC (SEQ ID NO:76), CAHAVC (SEQ ID NO:12), CAHAVDC (SEQ ID NO:13), CAHAVDIC (SEQ ID NO:14), CRAHAVDC (SEQ ID NO:15), CLRAHAVDC (SEQ ID NO:16), DHAVK (SEQ ID NO:17), KHAVE (SEQ ID NO:18) or AHAVDI (SEQ ID NO:19). Derivatives of such peptides, in which the N- and/or C-terminal functional groups are modified as also preferred, such as N-Ac-CHAVC-NH$_2$ (SEQ ID NO:10), N-Ac-CHAVDC-NH$_2$ (SEQ ID NO:20), N-Ac-CHAVDIC-NH$_2$ (SEQ ID NO:50), N-Ac-CHAVDINC-NH$_2$ (SEQ ID NO:51), N-Ac-CHAVDINGC-NH$_2$ (SEQ ID NO:76), N-Ac-CAHAVC-NH$_2$ (SEQ ID NO:22), N-Ac-CAHAVDC-NH$_2$ (SEQ ID NO:26), N-Ac-CAHAVDIC-NH$_2$ (SEQ ID NO:24), N-Ac-CRAHAVDC-NH$_2$ (SEQ ID NO:28), N-Ac-CLRAHAVDC-NH$_2$ (SEQ ID NO:32), N-Ac-DHAVK-NH$_2$ (SEQ ID NO:14), N-Ac-KHAVE-NH$_2$ (SEQ ID NO:16) and N-Ac-AHAVDI-NH$_2$ (SEQ ID NO:34), as well as peptides without the N-acetyl group. In addition, a modulating agent comprising RGD and/or YIGSR (SEQ ID NO:52), which are bound by integrins, the cadherin CAR sequence HAV, and/or the N-CAM CAR sequence KYSFNYDGSE (SEQ ID NO:53) may further facilitate neurite outgrowth. Other preferred CAR sequences are the OB-cadherin CAR sequences, as well as dsc and dsg CAR sequences provided herein. Modulating agents comprising antibodies, or fragments thereof, may be used within this aspect of the present invention without the use of linkers or support materials. Preferred antibody modulating agents include Fab fragments directed against the N-cadherin CAR sequence FHLRAHAVDINGNQV-NH$_2$ (SEQ ID NO:75). Fab fragments directed against the N-CAM CAR sequence KYSFNYDGSE (SEQ ID NO:53) may also be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

The following examples are offered by way of illustration and not by way of limitation.

EXAMPLE 1

Preparation of Representative Cyclic Pepides

This Example illustrates the solid phase synthesis of representative cyclic peptides.

The peptides were assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the a-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

EXAMPLE 2

Disruption of the Ability of Mouse Cerebellar Neurons to Extend Neurites

Three cell adhesion molecules, N-cadherin, N-CAM and L1, are capable of regulating neurite outgrowth (Doherty and Walsh, Curr. Op. Neurobiol. 4:49–55, 1994; Williams et al., Neuron 13:583–594, 1994; Hall et al., Cell Adhesion and Commun. 3:441–450, 1996; Doherty and Walsh, Mol. Cell. Neurosci. 8:99–111, 1994; Safell et al., Neuron 18:231–242, 1997). Neurons cultured on monolayers of 3T3 cells that have been transfected with cDNAs encoding N-cadherin, N-CAM or L1 extend longer neurites than neurons cultured on 3T3 cells not expressing these cell adhesion molecules. This Example illustrates the use of a representative cyclic peptide to inhibit neurite outgrowth.

Neurons were cultured on monolayers of 3T3 cells transfected with cDNA encoding N-cadherin essentially as described by Doherty and Walsh, Curr. Op. Neurobiol. 4:49–55, 1994; Williams et al., Neuron 13:583–594, 1994; Hall et al., Cell Adhesion and Commun. 3:441–450, 1996; Doherty and Walsh, Mol. Cell. Neurosci. 8:99–111, 1994; Safell et al., Neuron 18:231–242, 1997. Briefly, monolayers of control 3T3 fibroblasts and 3T3 fibroblasts that express N-cadherin were established by overnight culture of 80,000 cells in individual wells of an 8-chamber well tissue culture slide. 3000 cerebellar neurons isolated from post-natal day 3 mouse brains were cultured for 18 hours on the various monolayers in control media (SATO/2%FCS), or media supplemented with various concentrations of the cyclic peptide N-Ac-CHAVC-NH$_2$ (SEQ ID NO:10) or a control peptide without the HAV sequence (N-Ac-CHGVC-NH$_2$; SEQ ID NO:11). The cultures were then fixed and stained for GAP43 which specifically binds to the neurons and their neurites. The length of the longest neurite on each GAP43 positive neuron was then measured by computer assisted morphometry.

Figure 8:
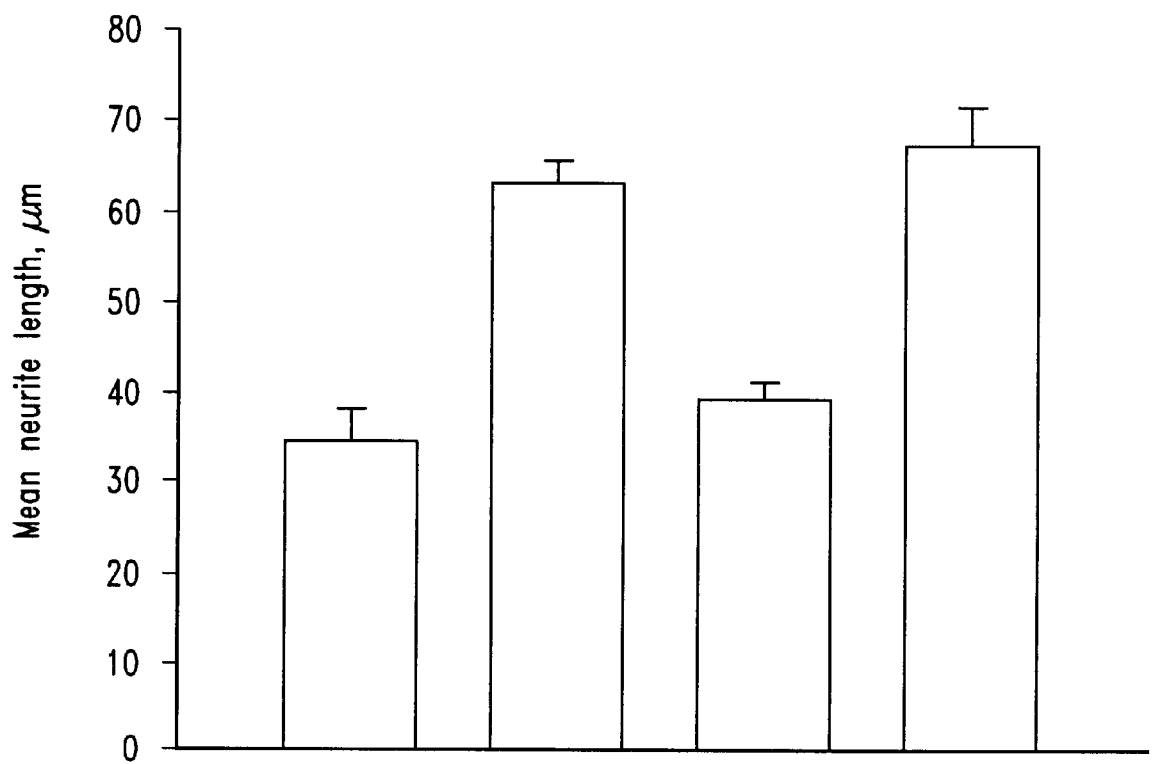

As shown in FIG. 8, culture for 18 hours with N-Ac-CHAVC-NH$_2$ (SEQ ID NO:10) at a concentration of 500 µg/mL inhibited neurite outgrowth on 3T3 cells expressing N-cadherin, whereas the cyclic peptide N-Ac-CHGVC-NH$_2$ (SEQ ID NO:11; also at a concentration of 500 µg/ml) had no effect on this process. Furthermore, the cyclic peptide N-Ac-CHAVC-NH$_2$ (SEQ ID NO:10; used at a concentration of 500 µg/ml) did not inhibit neurite outgrowth on 3T3 cells not expressing N-cadherin, N-CAM, or L1 (control cells), thus indicating that the peptide is not toxic and that it has no non-specific effects on neurite outgrowth (FIG. 8). These data also indicate that the peptide does not effect integrin function.

Figure 4:
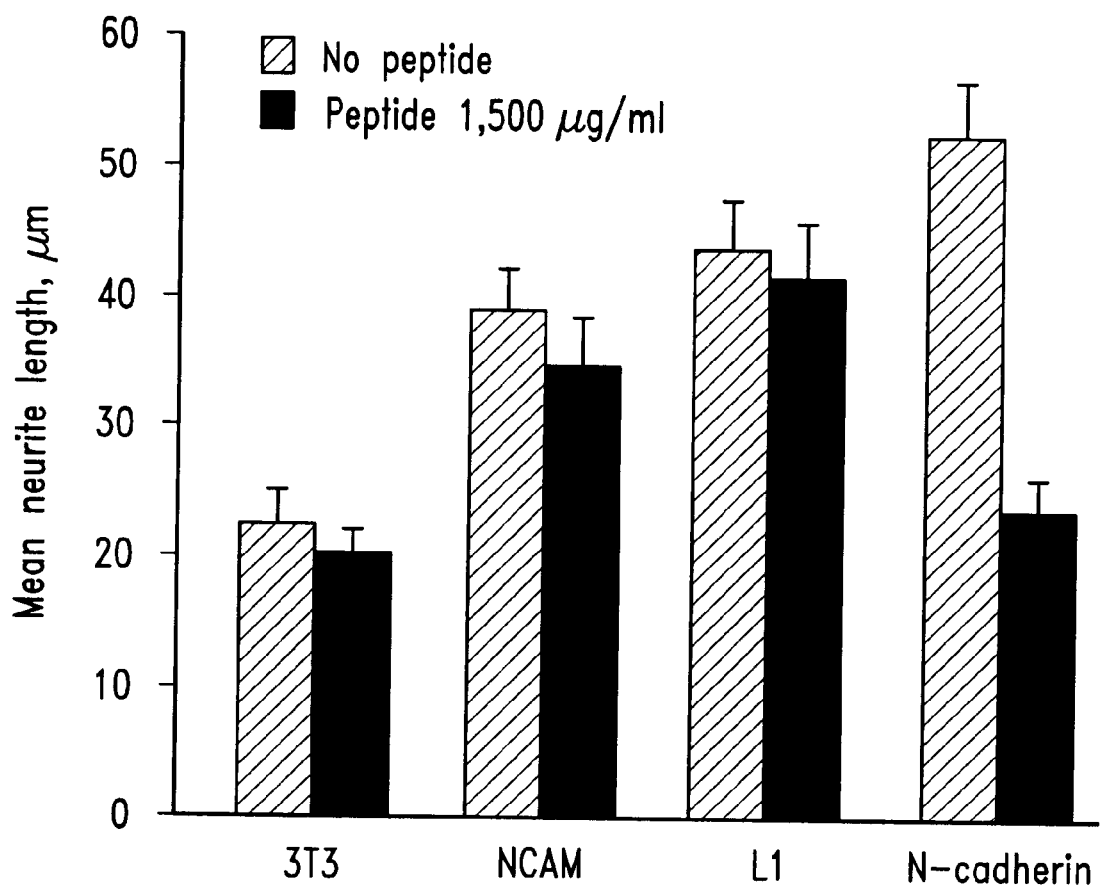
Figure 5:
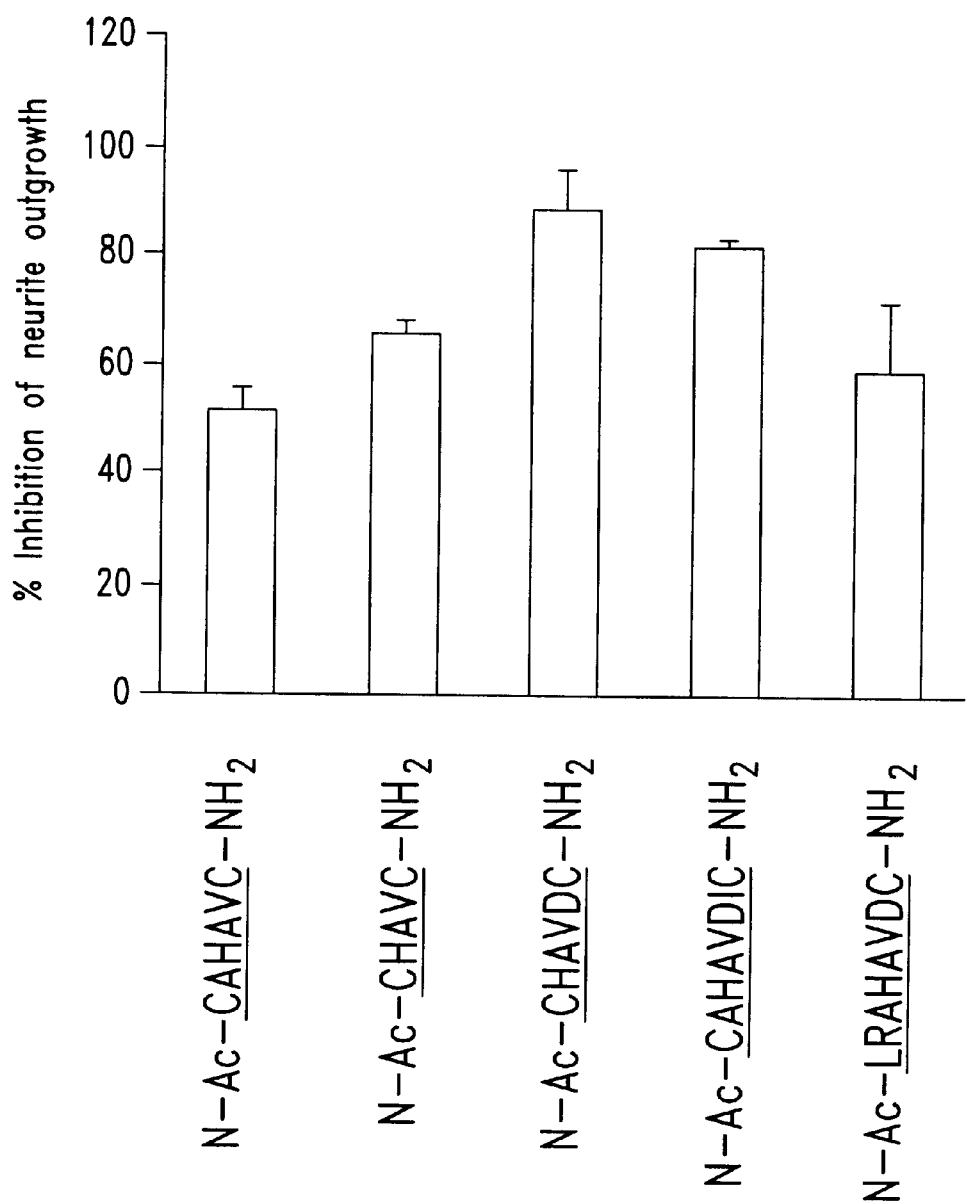
Figure 9:
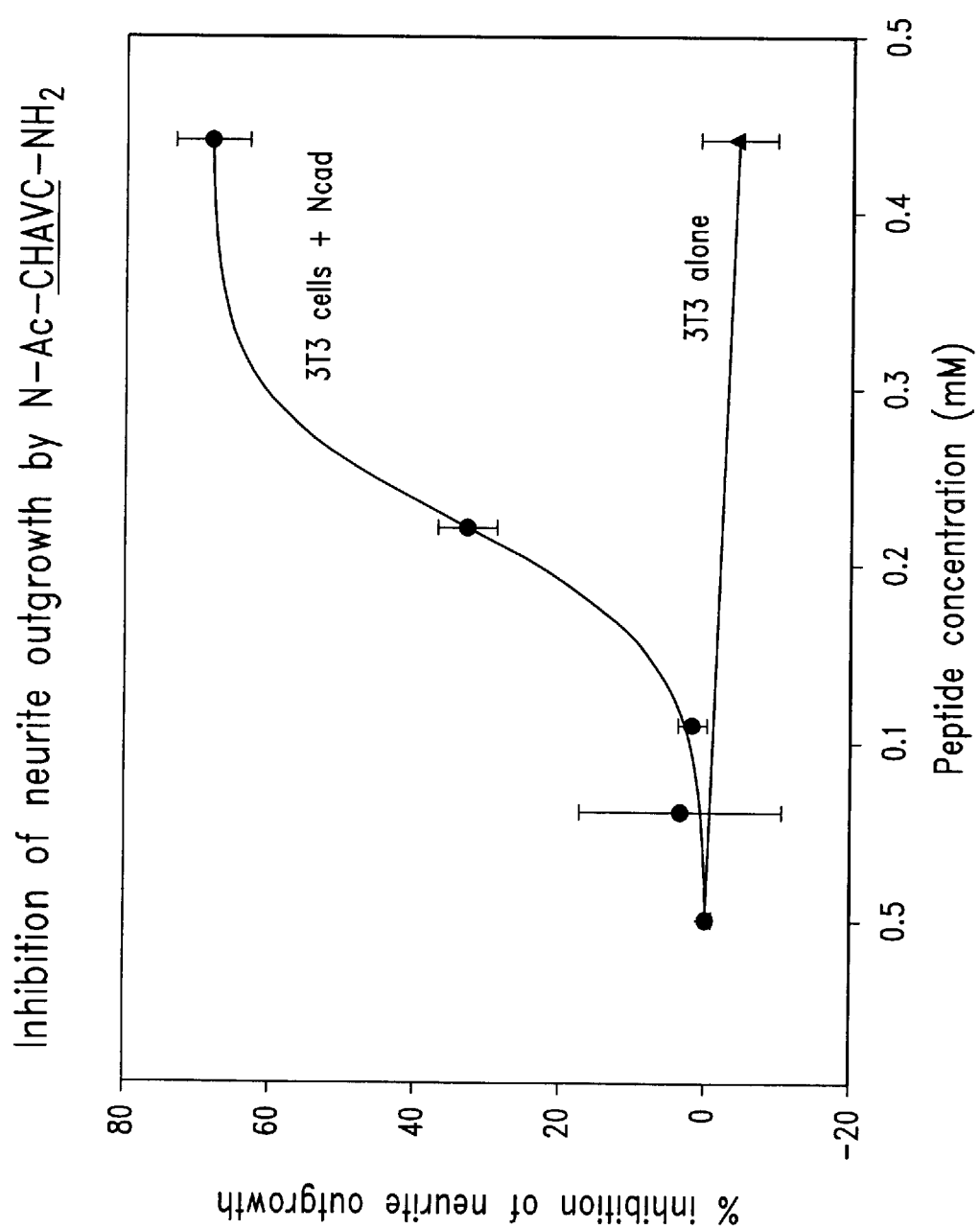

A dose-response study demonstrated that N-Ac-CHAVC-NH$_2$ (SEQ ID NO:10) significantly inhibited neurite outgrowth on 3T3 cells expressing N-cadherin at a concentration of 50 µg/mL, and completely inhibited neurite outgrowth on these cells at a concentration of 500 µg/mL (FIG. 9). Finally, N-Ac-CHAVC-NH$_2$ (SEQ ID NO:10; used at a concentration of 500 µg/mL) did not inhibit neurite outgrowth on 3T3 cells expressing either N-CAM or L1 (FIG. 4). These results indicate that the peptide N-Ac-CHAVC-NH$_2$ (SEQ ID NO:10) specifically inhibits the function of N-cadherin. Collectively, the results obtained from these studies demonstrate that N-Ac-CHAVC-NH$_2$ (SEQ ID NO:10) is an effective inhibitor of neurite outgrowth by virtue of its ability to disrupt N-cadherin function.

EXAMPLE 3

Use of Flanking Sequences to Influence Cadherin Receptor Specificity

This Example illustrates the effect of sequences that flank the HAV sequence on specificity for N-cadherin-mediated responses.

A series of cyclic peptide modulating agents was tested for their ability to inhibit neurite outgrowth. Certain peptides were non-selective (i.e., not specific for a particular cadherin), while others were designed to incorporate flanking sequences of N-cadherin or E-cadherin. The percentage inhibition of neurite outgrowth for each compound (at 250 µg/mL) was then evaluated as described in Example 2, except that neurons were isolated from rats, rather than mice.

Cell culture and neurite outgrowth assays. Co-cultures of cerebellar neurons on monolayers of control 3T3 cells and monolayers of transfected 3T3 cells that express physiological levels of chick N-cadherin or human L1 were established as previously described (Williams et al., Neuron 13:583–594, 1994). In brief, 80,000 3T3 cells (control and transfected) were plated into individual chambers of an eight-chamber tissue culture slide coated with polylysine and fibronectin and cultured in DMEM/10%FCS. After 24 hours, when confluent monolayers had formed, the medium was removed and 3000 cerebellar neurons isolated from post-natal day 2–3 rats were plated into each well in SATO media (Doherty et al., Nature 343:464–466, 1990) supplemented with 2%FCS. All of the test peptides were added immediately before the neurons as a 2X stock prepared in SATO/2%FCS. The co-cultures were maintained for 16–18 hours, at which time they were fixed and immunostained for GAP-43 which is present only in the neurons and delineates the neuritic processes. The mean length of the longest neurite per cell was measured for 150–200 neurons sampled in replicate cultures as previously described (Williams et al., Neuron 13:583–594, 1994). The percentage inhibition of neurite outgrowth at various peptide concentrations was calculated as the average of at least three independent experiments. Dose-response curves were evaluated and the $EC_{50}$ values determined.

Peptide Synthesis. All peptides were synthesized using the solid-phase method (Merrifield, Journal of the American Chemical Society 85:2149, 1963; Stewart and Young, (1969) Solid Phase Peptide Synthesis, W. H. Freeman, San Francisco). The peptides were assembled on methylbenzhydrylamine resin for the C-terminal amide peptides and the traditional Merrifield resins were used for the C-terminal acid peptides. Acetylation of the N-terminal was performed by reacting the peptide resins with a solution of acetic anhydride in dichloromethane in the presence of diisopropylethylamine after removal of the N-α-Boc by acidolysis using trifluoroacetic acid. All of the cyclic peptides bear the disulfide tether Cys-S-S-Cys. Cyclization was accomplished by reacting the side chain thiol functionalities of the two cysteine residues with a 10% solution of iodine in methanol.

All peptides with the exception of N-Ac-CHAVDIC-NH$_2$ (SEQ ID NO:50) were prepared as a stock solution at a concentration of 5–10 mg/ml in distilled water, and stored in small aliquots at −70° C. until needed. For solubility reasons N-Ac-CHAVDIC-NH$_2$ (SEQ ID NO:50) was made up in tissue culture DMSO at a concentration of 20 mg/mL.

Effects of cyclic HA V peptides on N-cadherin function. The ability of N-Ac-CHAVC-NH$_2$ (SEQ ID NO:10; compound 1) to inhibit neurite outgrowth was initially tested. This cyclic peptide has the cadherin CAR sequence (HAV) and no flanking amino acid residues. Neurons were cultured on confluent monolayers of control (untransfected) and N-cadherin expressing 3T3 cells for 16–18 hours. The cells were then fixed and the length of the longest neurite on 150–200 neurons was determined by standard assay, as described above. FIG. 8 gives the mean neurite length in a representative experiment where cerebellar neurons have been cultured over control and N-cadherin expressing cells. In the absence of peptide, the mean length of the longest neurite per cell was approximately double on the N-cadherin expressing cells, as compared to 3T3 cells. This response requires N-cadherin function in both the neuron and transfected fibroblast. FIG. 8 also illustrates inhibition of neurite outgrowth in neurons cultured over N-cadherin expressing cells in the presence of N-Ac-CHAVC-NH$_2$ (SEQ ID NO:10; compound 1, 500 µg/mL). In addition, the corresponding control peptide N-Ac-CHGVC-NH$_2$ (SEQ ID NO:11; compound 2, 500 µg/mL) had no effect on neurite outgrowth over N-cadherin expressing monolayers (FIG. 8).

FIG. 9 gives the pooled data from a number of experiments where the neurons have been cultured over control and N-cadherin expressing cells in the presence of increasing concentrations of N-Ac-CHAVC-NH$_2$ (SEQ ID NO:10; compound 1). This compound has no significant effect on the N-cadherin response at concentrations up to 62 µg/ml. A significant inhibition (33.2+/−4.0%) of the response was seen at a peptide concentration of 125 µg/ml (mean+/−s.e.m, n=3 independent experiments), with a more complete inhibition at 250 µg/ml. Results pooled from four independent experiments demonstrated a 68.2+/−5.1% inhibition of the N-cadherin response when the peptide was present at 250 µg/ml (see Table 9). An EC$_{50}$ value of 0.22 mM was obtained from the dose-response curve. In contrast to the effects of the peptide on neurite outgrowth over N-cadherin expressing cells, it had no significant effect on neurite extension over control 3T3 cells (FIG. 9). This observation demonstrates that N-Ac-CHAVC-NH$_2$ (SEQ ID NO:10) is capable of acting as an antagonist and inhibiting cadherin function. Additionally, N-Ac-CHAVC-NH$_2$ (SEQ ID NO:10) does not inhibit integrin receptor function, as the latter is required for neurite extension over 3T3 cells. Compound 1 alone elicits a biological response of similar potency to the linear 10-mer N-Ac-LPAHAVDING-NH$_2$ (SEQ ID NO:79; % inhibition at 250 mg/mL, 68.8+/−4.1). In contrast, compound 3, with a free amino group at the N-terminal region, was inactive (Table 9).

Peptides included in Table 9 are placed into one of three groups. The first group, comprising compounds 1 and 3 can be viewed as potential general or non-specific cadherin inhibitors. The second group, which includes compounds 23, 25, 27, 29, and 31, were designed as putative E-cadherin specific inhibitors by incorporation of flanking amino acids from the HAV region of native human E-cadherin. The remaining HAV-containing compounds were designed as putative N-cadherin inhibitors by virtue of their HAV flanking amino acids being derived from the native human N-cadherin sequence.

Figure 10:
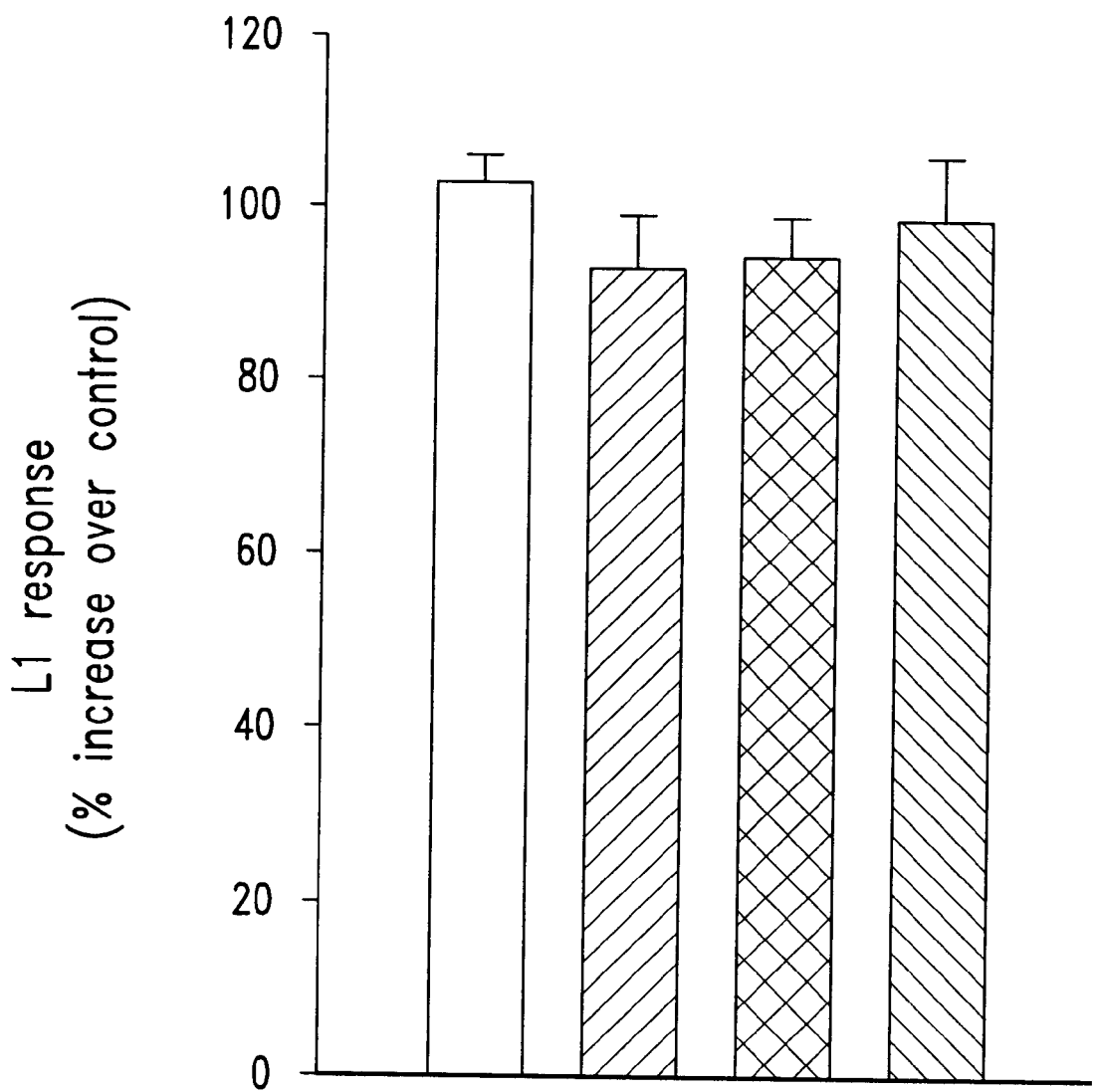

Placement of amino acids derived from the N-cadherin sequence on the N-terminus of the HAV sequence appears to either have little affect (compound 7, N-Ac-CAHAVC-NH$_2$; SEQ ID NO:22) or a detrimental affect (e.g., compound 17, N-Ac-CLRAHAVC-NH$_2$; SEQ ID NO:30) on activity. In contrast, addition of an aspartic acid residue on the C-terminus (compound 5, N-Ac-CHAVDC-NH$_2$; SEQ ID NO:20) dramatically increased the inhibitory activity of the peptides (Table 5). Addition of amino acid residues on the N-terminus of the CAR sequence in compound 5 (compound 11, N-Ac-CAHAVDC-NH$_2$, SEQ ID NO:26; compound 17, N-Ac-CRAHAVDC-NH$_2$; SEQ ID NO:28) completely eliminated inhibitory activity. Addition of a second amino acid on the C-terminus (Ile) to yield N-Ac-CHAVDIC-NH$_2$ (compound 33; SEQ ID NO:50) further increased activity from that found for compound 5 and addition of an amino acid to the N-terminus (compound 13, N-Ac-CAHAVDIC-NH$_2$; SEQ ID NO:24) reduced, but did not eliminate, the activity. Again, removal of the N-terminus blocking group to yield H-CAHAVDIC-NH$_2$ (compound 11; SEQ ID NO:24) resulted in total loss of activity. Further extension of the C-terminus to yield N-Ac-CHAVDINC-NH$_2$ (compound 34; SEQ ID NO:51) resulted in only a slight loss in activity as exemplified by the small difference in the EC$_{50}$ values for these two compounds (Table 6). A further addition of a glycine residue (compound 35, N-Ac-CHAVDINGC-NH$_2$ (SEQ ID NO:76) completely abrogates activity. Furthermore, the most active N-cadherin antagonists (N-Ac-CHAVDIC-NH$_2$ (SEQ ID NO:50) EC$_{50}$= 0.060 mM, N-Ac-CHAVDINC-NH$_2$ (SEQ ID NO:51), EC$_{50}$=0.070 mM and N-Ac-CHAVDC-NH$_2$ (SEQ ID NO:20), EC$_{50}$=0.093 mM) did not interfere with the ability of neurons to extend neurites over 3T3 cells expressing L1 at concentrations that substantially inhibited the N-cadherin response (FIG. 10).

TABLE 5

Effects of Non-Specific, N-Cadherin Specific and E-Cadherin Specific Antagonists on N-Cadherin Dependent Neurite Outgrowth

| Test Peptide (250 µg/mL) | ID | % Inhibition | Control Peptide (250 µg/mL) | ID | % Inhibition |
|---|---|---|---|---|---|
| Non-Specific | | | | | |
| 1. N—Ac—CHAVC—NH$_2$ | 10 | 68.2 ± 5.1 (4) | 2. N—Ac—CHGVC—NH$_2$ | 11 | 4.8 ± 5.3 |
| 3. H—CHAVC—NH$_2$ | 10 | 1.7 ± 1.1 (3) | 4. H—CHGVC—NH$_2$ | 11 | 7.8 ± 7.1 |
| N-cadherin Specific | | | | | |
| 5. N—Ac—CHAVDC—NH$_2$ | 20 | 88.4 ± 3.7 (3) | 6. N—Ac—CHGVDC—NH$_2$ | 21 | −8.6 ± 5.8 |
| 7. N—Ac—CAHAVC—NH$_2$ | 22 | 58.5 ± 1.0 (3) | 8. N—Ac—CAHGVC—NH$_2$ | 23 | −6.4 ± 5.6 |
| 9. N—Ac—CAHAVDC—NH$_2$ | 26 | 13.3 ± 8.3 (3) | 10. N—Ac—CAHGVDC—NH$_2$ | 27 | 4.0 ± 6.9 |
| 11. H—CAHAVDC—NH$_2$ | 26 | 1.3 ± 13.0 (3) | 12. H—CAHGVDC—NH$_2$ | 27 | 5.7 ± 7.8 |
| 13. N—Ac—CAHAVDIC—NH$_2$ | 24 | 89.4 (2) | 14. N—Ac—CAHGVDIC—NH$_2$ | 25 | 4.8 ± 6.5 |

TABLE 5-continued

Effects of Non-Specific, N-Cadherin Specific and E-Cadherin Specific Antagonists on N-Cadherin Dependent Neurite Outgrowth

| Test Peptide (250 µg/mL) | ID | % Inhibition | Control Peptide (250 µg/mL) | ID | % Inhibition |
|---|---|---|---|---|---|
| 15. H—CAHAVDIC—NH$_2$ | 24 | −3.7 ± 2.9 (3) | 16. H—CAHGVDIC—NH$_2$ | 25 | 7.2 ± 8.1 |
| 17. N—Ac—CLRAHAVC—NH$_2$ | 30 | 9.9 ± 6.6 (3) | 18. N—Ac—CLRAHGVC—NH$_2$ | 31 | −0.5 ± 7.1 |
| 19. N—Ac—CRAHAVDC—NH$_2$ | 28 | −5.0 ± 4.9 (3) | 20. N—Ac—CRAHGVDC—NH$_2$ | 29 | −8.0 ± 6.0 |
| 21. N—Ac—CLRAHAVDC—NH$_2$ | 32 | 76.3 ± 6.6 (3) | 22. N—Ac—CLRAHGVDC—NH$_2$ | 33 | −6.8 ± 6.2 |
| E-cadherin Specific 39 | | | | | |
| 23. N—Ac—CSHAVC—NH$_2$ | 36 | 11.0 ± 8.6 | 24. N—Ac—CSHGVC—NH$_2$ | 37 | 12.5 ± 7.5 |
| 25. N—Ac—CHAVSC—NH$_2$ | 38 | −2.5 ± 7.4 | 26. N—Ac—CHGVSC—NH$_2$ | 39 | −6.7 ± 5.8 |
| 27. N—Ac—CSHAVSC—NH$_2$ | 40 | 8.3 ± 7.3 | 28. N—Ac—CSHGVSC—NH$_2$ | 41 | 10.8 ± 7.6 |
| 29. N—Ac—CSHAVSSC—NH$_2$ | 42 | −12.6 ± 6.4 | 30. N—Ac—CSHGVSSC—NH$_2$ | 43 | −5.6 ± 5.9 |
| 31. N—Ac—CHAVSSC—NH$_2$ | 44 | 34.4 ± 11.3 (3) | 32. N—Ac—CHGVSSC—NH$_2$ | 45 | 14.8 ± 6.5 |

Structure/Activity Relationships for the Inhibition of Neurite Outgrowth with Cyclic HAV-Containing Peptides. In order to further assess the effects of modifying the amino acids flanking the HAV sequence on receptor selectivity, a series of HAV-containing peptides were evaluated for their ability to inhibit neurite outgrowth. These peptides correspond to cyclized sequences derived from the human N-cadherin (RFHLRAHAVDINGN; SEQ ID NO:80) and E-cadherin (TLFSHAVSSNGN; SEQ ID NO:81) sequences immediately adjacent to the surrounding the active site (HAV).

Figure 11:
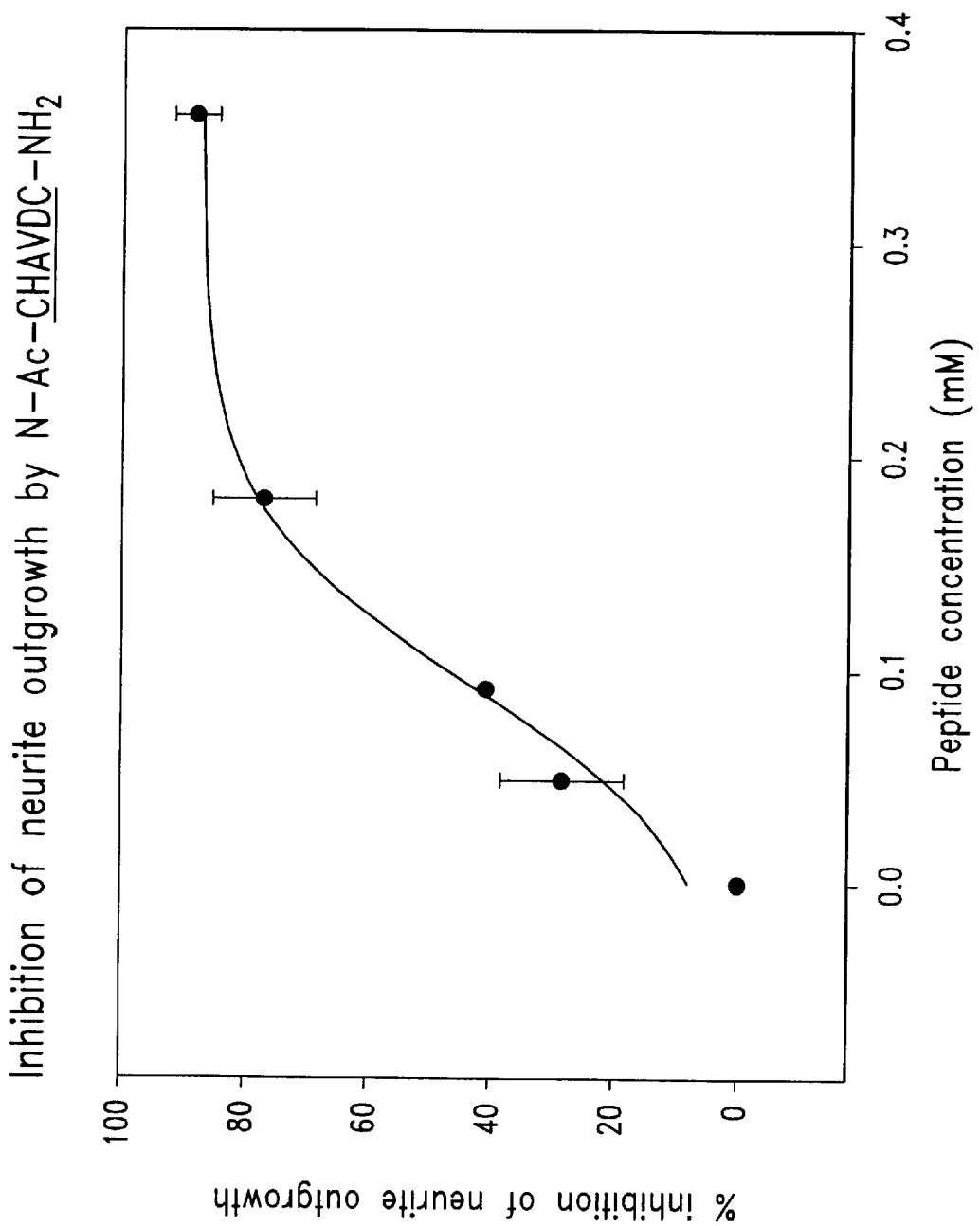
Figure 12:
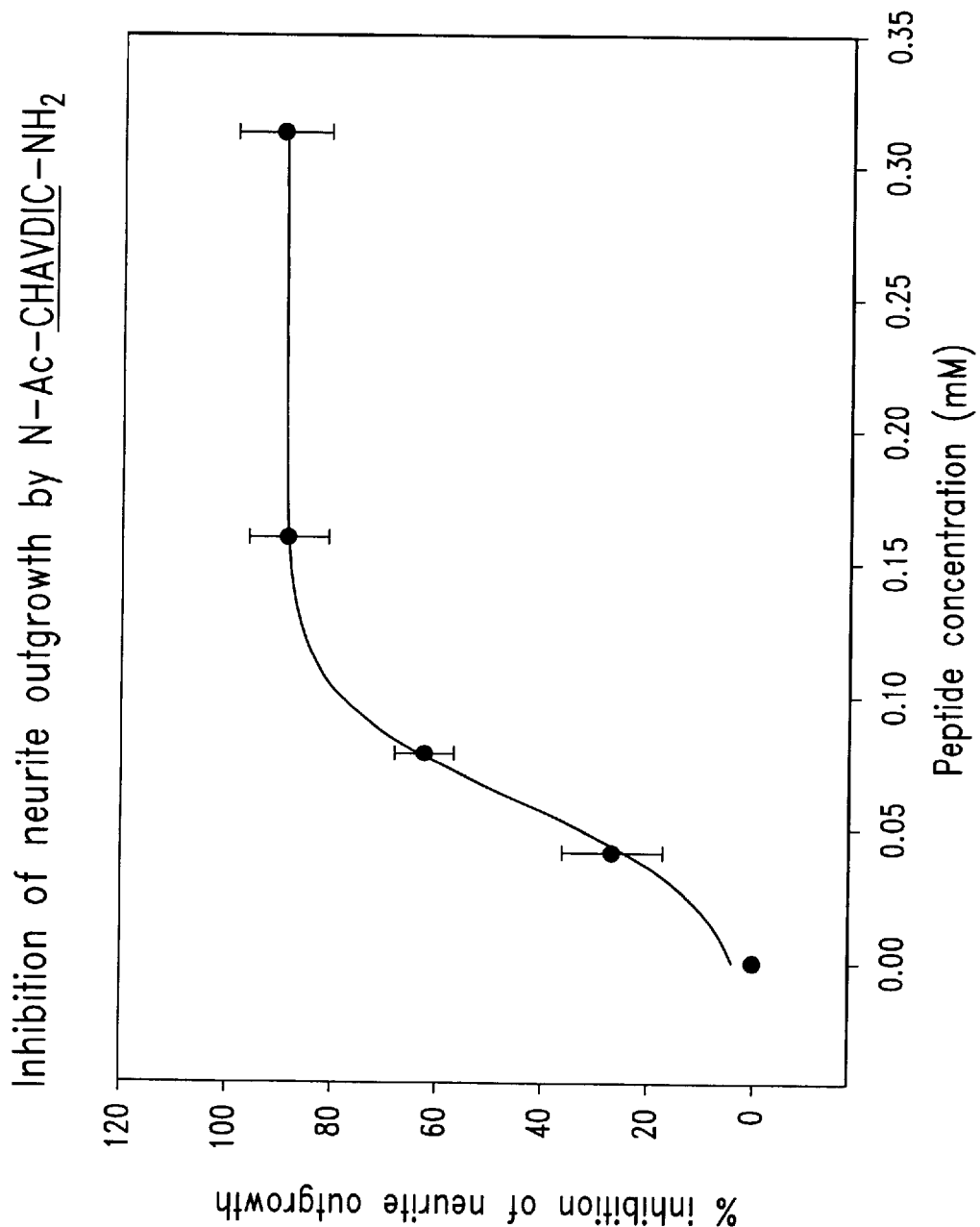
Figure 13:
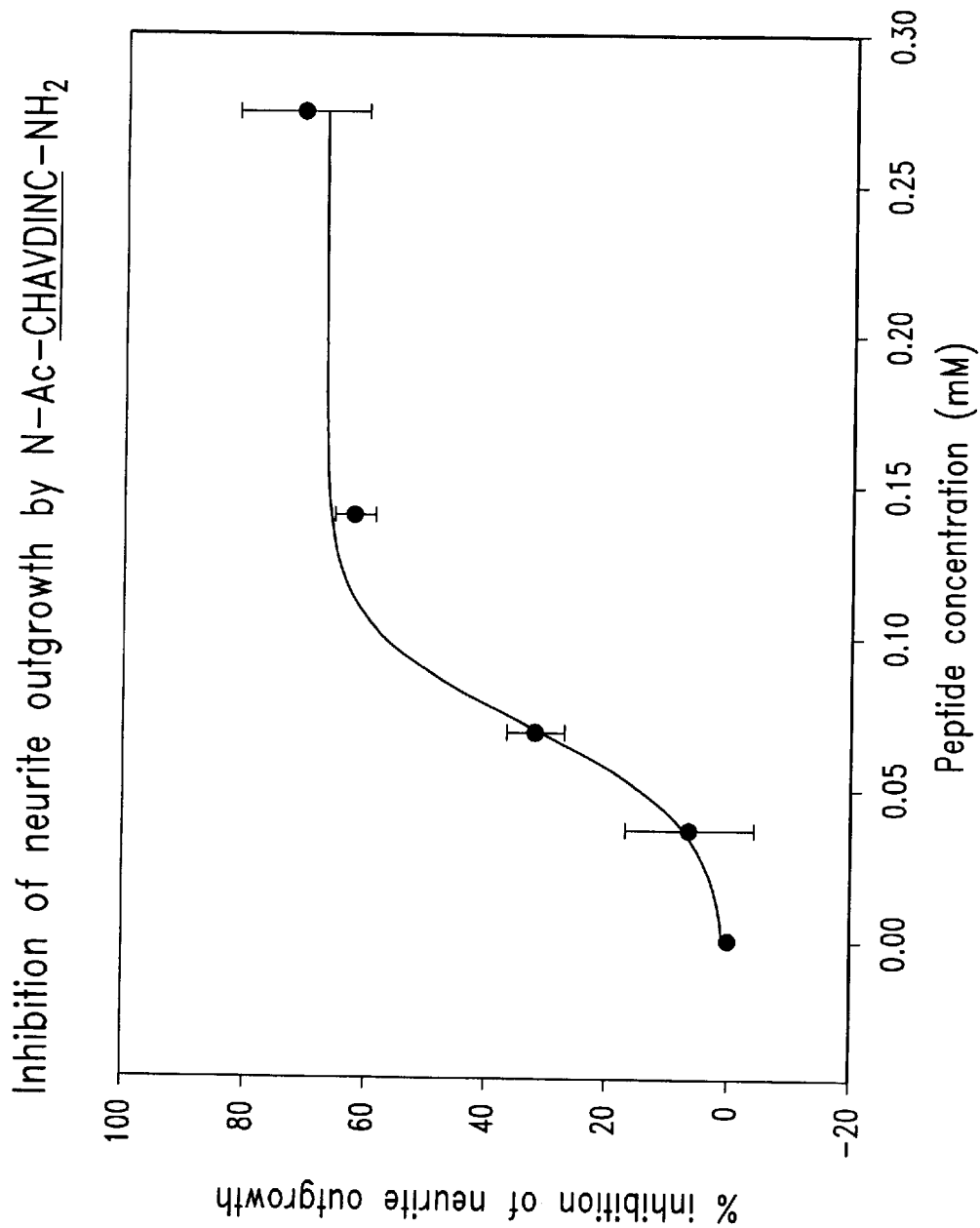

The results shown in Table 5 identify four "N-cadherin" peptides (N-Ac-CHAVDC-NH$_2$ (compound 5; SEQ ID NO:20), N-Ac-CAHAVC-NH$_2$ (compound 7; SEQ ID NO:22), N-Ac-CAHAVDIC-NH$_2$ (compound 13; SEQ ID NO:24) and N-Ac-CLRAHAVDC-NH$_2$ (compound 21; SEQ ID NO:32)) which are potent inhibitors of neurite outgrowth when used at a concentration of 250 µg/mL. All of these peptides except peptide N-Ac-CHAVDC-NH$_2$ (SEQ ID NO:20) lost activity at concentrations of 125 mg/mL or below. A dose response curve (FIG. 11) for N-Ac-CHAVDC-NH$_2$ (SEQ ID NO:20) indicated that significant activity remained at 33 µg/mL (% inhibition 28.5+/−10) and an EC$_{50}$ value of 0.093 mM was obtained. These results indicated that the aspartic acid on the carboxy terminus of the HAV motif was likely a key residue for N-cadherin receptor binding. To further explore the influence of the C-terminus residues on activity, N-Ac-CHAVDIC-NH$_2$ (compound 33; SEQ ID NO:50), N-Ac-CHAVDINC-NH$_2$ (compound 34; SEQ ID NO:51) and N-Ac-CHAVDINGC-NH$_2$ (compound 35; SEQ ID NO:76) were synthesized. Both N-Ac-CHAVDIC-NH$_2$ (SEQ ID NO:50) and N-Ac-CHAVDINC-NH$_2$ (SEQ ID NO:51) turned out to be potent inhibitors (Table 6) and dose response curves for these two compounds yield EC$_{50}$ values of 0.060 mM (FIG. 12) and 0.070 mM (FIG. 13), respectively.

TABLE 6

Effect of Additional C-terminal Residues on Neurite Outgrowth

| Test Peptide (125 µg/mL) | SEQ ID | % Inhibition | EC$_{50}$ (mM) |
|---|---|---|---|
| 5. N—Ac—CHAVDC—NH$_2$ | 20 | 77.1 ± 8.4 | 0.093 |
| 33. N—Ac—CHAVDIC—NH$_2$ | 50 | 88.3 ± 7.5 | 0.060 |
| 34. N—Ac—CHAVDINC—NH$_2$ | 51 | 62.0 ± 3.4 | 0.070 |
| 35. N—Ac—CHAVDINGC—NH$_2$ | 76 | 1.5 ± 2.2 | |

Interestingly, flanking of the HAV motif with amino acids found in human E-cadherin sequence resulted in either a complete (peptides 23, 25, 27 and 29) or substantial (peptide 31) reduction in inhibitory activity (Table 5). In addition, a series of corresponding control peptides, in which the HAV sequence had been replaced by HGV, were also tested in the screen. All sixteen control peptides failed to inhibit the N-cadherin response (see Table 5). Finally, if the N-terminal blocking group was removed these peptides lost activity (Table 5, compounds 3, 15).

Effects of HAV-containing peptides on the L1 response. Other cell adhesion molecules, such as L1, can stimulate neurite outgrowth, and this response shares the same downstream signaling steps as the N-cadherin response. In order to ascertain the specificity of the most active N-cadherin antagonists (N-Ac-CHAVDC-NH$_2$ (compound 5; SEQ ID NO:20), N-Ac-CHAVDIC-NH$_2$ (compound 33; SEQ ID NO:50) and N-Ac-CHAVDINC-NH$_2$ (compound 34; SEQ ID NO:51), cerebellar neurons were cultured over either control 3T3 cell monolayers, or monolayers of 3T3 cells stably transfected with cDNA encoding L1 in the presence and absence of each peptide. As previously reported, L1 stimulated neurite outgrowth from cerebellar neurons. This response was not inhibited by any of the above cyclic peptides at concentrations that prevented N-cadherin-mediated neurite outgrowth (FIG. 10).

These results demonstrate that cyclic HAV peptides containing flanking amino acids found in N-cadherin are potent inhibitors of neurite outgrowth, whereas cyclic HAV-containing peptides containing flanking amino acids found in E-cadherin are inactive for such purposes. In addition, specificity for the N-cadherin receptor can be built into the peptides by adding flanking amino acids derived from native N-cadherin to the C-terminus, while addition of one or two amino acid residues on the N-terminus appears to be detrimental to activity (addition of a third amino acid on the N-terminus to give N-Ac-CLRAHAVDC[<m]xNH$_2$ (compound 21; SEQ ID NO:43) resulted in partial recovery of activity). Collectively, these results show that the information needed for "non-specific" cadherin binding resides in the HAV sequence, whereas the role of the surrounding amino acids is to "constrain" the side chains of His and Val into a conformation required for "specific" cadherin (e.g., N-cadherin) recognition.

EXAMPLE 4

Toxicity and Cell Proliferation Studies

This Example illustrates the initial work to evaluate the cytotoxic effects of representative cyclic peptides.

N-Ac-CHAVC-NH$_2$ (SEQ ID NO:10) and the control peptide N-Ac-CHGVC-NH$_2$ (SEQ ID NO:11) were evaluated for possible cytotoxic effects on human microvascular endothelial (HMVEC; Clonetics), human umbilical vein endothelial (HUVEC; ATCC #CRL-1730), IAFp2 (human fibroblast cell line; Institute Armand-Frapier, Montreal, Quebec), WI-38 (human fibroblast cell line; ATCC #CCL-75), MDA-MB231 (human breast cancer cell line; ATCC #HTB-26), and PC-3 (human prostate cancer cell line; ATCC #CRL-1435) cells utilizing the MTT assay (Plumb et al., Cancer Res. 49:4435–4440, 1989). Neither of the peptides was cytotoxic at concentrations up to and including 100 μM. Similarly, neither of the peptides was capable of inhibiting the proliferation of the above cell lines at concentrations up to 100 μM, as judged by $^3$H-thymidine incorporation assays.

In fact, none of the compounds tested thus far show any cytotoxicity at concentrations up to and including 100 μM (Tables 7 and 8). However, N-Ac-CHAVSC-NH$_2$ (SEQ ID NO:38), N-Ac-CHGVSC-NH$_2$ (SEQ ID NO:39), N-Ac-CVAHC-NH$_2$ (SEQ ID NO:18), N-Ac-CVGHC-NH$_2$ (SEQ ID NO:19) and N-Ac-CSHAVSSC-NH$_2$ (SEQ ID NO:42) inhibited the proliferation of HUVEC at concentrations (IC$_{50}$ values) of 57 μM, 42 μM, 8 μM, 30 μM and 69 μM respectively, as judged by $^3$H-thymidine incorporation assays. N-Ac-CSHAVSSC-NH$_2$ (SEQ ID NO:42) also inhibited the proliferation of MDA-MB231 cells at a concentration of 76 μM and HMVEC cells at a concentration of 70 μM (Tables 7 and 8). N-Ac-CHAVSC-NH$_2$ (SEQ ID NO:38) inhibited the proliferation of MDA-MB231 cells at a concentration of 52 μM.

TABLE 7

Evaluation of Peptides for Cytotoxicity and Capacity to Inhibit Cell Proliferation of Normal Cells (IC$_5$0 in μM)

| | | Normal Cells | | | | | | | |
|---|---|---|---|---|---|---|---|---|---|
| | | HMVEC | | HUVEC | | IAFp2 | | WI-38 | |
| Peptide | SEQ ID NO. | Cell prol | Cytotox | Cell prol | Cytotox | Cell prol | Cytotox | Cell prol | Cytotox |
| N—Ac—CHGVC—NH$_2$ (control for #1) | 11 | >100 μM | >100 μM | >100 μM | >100 μM | >100 μM | >100 μM | >100 μM | >100 μM |
| N—Ac—CHAVC—NH$_2$ (#1) | 10 | >100 μM | >100 μM | >100 μM | >100 μM | >100 μM | >100 μM | >100 μM | >100 μM |
| H—CHGVC—NH$_2$ (control for #2) | 11 | >100 μM | >100 μM | >100 μM | >100 μM | >100 μM | >100 μM | >100 μM | >100 μM |
| H—CHAVC—NH$_2$ (#2) | 10 | >100 μM | >100 μM | >100 μM | >100 μM | >100 μM | >100 μM | >100 μM | >100 μM |
| N—Ac—CHGVSC—NH$_2$ (control for #18) | 39 | >100 μM | >100 μM | 42 μM | >100 μM | >100 μM | >100 μM | >100 μM | >100 μM |
| N—Ac—CHAVSC—NH$_2$* (#18) | 38 | >100 μM | >100 μM | 57 μM | >100 μM | >100 μM | >100 μM | >100 μM | >100 μM |
| N—Ac—CSHGVC—NH$_2$ (control for #16) | 37 | >100 μM | >100 μM | >100 μM | >100 μM | >100 μM | >100 μM | >100 μM | >100 μM |
| N—Ac—CSHAVC—NH$_2$ (#16) | 36 | >100 μM | >100 μM | >100 μM | >100 μM | >100 μM | >100 μM | >100 μM | >100 μM |
| N—Ac—CAHGVDC—NH$_2$ (control for #22) | 27 | >100 μM | >100 μM | >100 μM | >100 μM | >100 μM | >100 μM | >100 μM | >100 μM |
| N—Ac—CAHAVDC—NH$_2$ (#22) | 26 | >100 μM | >100 μM | >100 μM | >100 μM | >100 μM | >100 μM | >100 μM | >100 μM |
| N—Ac—KHGVD—NH$_2$ (control for #26) | 13 | >100 μM | >100 μM | >100 μM | >100 μM | >100 μM | >100 μM | >100 μM | >100 μM |
| N—Ac—KHAVD—NH$_2$ (#26) | 12 | >100 μM | >100 μM | >100 μM | >100 μM | >100 μM | >100 μM | >100 μM | >100 μM |
| H—CAHGVDC—NH$_2$ (control for #45) | 27 | >100 μM | >100 μM | >100 μM | >100 μM | >100 μM | >100 μM | >100 μM | >100 μM |
| H—CAHAVDC—NH$_2$ (#45) | 26 | >100 μM | >100 μM | >100 μM | >100 μM | >100 μM | >100 μM | >100 μM | >100 μM |
| H—CAHGVDIC—NH$_2$ (control for #47) | 25 | >100 μM | >100 μM | >100 μM | >100 μM | >100 μM | >100 μM | >100 μM | >100 μM |
| H—CAHAVDIC—NH$_2$ (#47) | 24 | >100 μM | >100 μM | >100 μM | >100 μM | >100 μM | >100 μM | >100 μM | >100 μM |
| N—Ac—CVGHC—NH$_2$ (control for #32) | 19 | >100 μM | >100 μM | 30 μM | >100 μM | >100 μM | >100 μM | >100 μM | >100 μM |
| N—Ac—CVAHC—NH$_2$ (#32) | 18 | >100 μM | >100 μM | 8 μM | >100 μM | >100 μM | >100 μM | >100 μM | >100 μM |
| N—Ac—CAHGVDIC—NH$_2$ (control for #14) | 25 | >100 μM | >100 μM | >100 μM | >100 μM | >100 μM | >100 μM | >100 μM | >100 μM |
| N—Ac—CAHAVDIC—NH$_2$ (#14) | 24 | >100 μM | >100 μM | >100 μM | >100 μM | >100 μM | >100 μM | >100 μM | >100 μM |
| N—Ac—CSHGVSSC—NH$_2$ (control for #24) | 43 | >100 μM | >100 μM | >100 μM | >100 μM | >100 μM | >100 μM | >100 μM | >100 μM |
| N—Ac—CSHAVSSC—NH$_2$* (#24) | 42 | 70 μM | >100 μM | 69 μM | >100 μM | >100 μM | >100 μM | >100 μM | >100 μM |

*Incompletely soluble in RPMI at 1 mM

TABLE 8

Evaluation of Peptides for Cytotoxicity and Capacity to Inhibit Cell Proliferation of Tumoral Cells (IC$_5$0 in μM)

| Peptide | SEQ ID NO: | Tumoral Cells | | | |
|---|---|---|---|---|---|
| | | MDA-MB231 | | PC-3 | |
| | | Cell Prol | Cytotox | Cell Prol | Cytotox |
| N—Ac—CHGVC—NH$_2$ (control for #1) | 11 | >100 μM | >100 μM | >100 μM | >100 μM |
| N—Ac—CHAVC—NH$_2$ (#1) | 10 | >100 μM | >100 μM | >100 μM | >100 μM |
| H—CHGVC—NH$_2$ (control for #2) | 11 | >100 μM | >100 μM | >100 μM | >100 μM |
| H—CHAVC—NH$_2$ (#2) | 10 | >100 μM | >100 μM | >100 μM | >100 μM |
| N—Ac—CHGVSC—NH$_2$ (control for #18) | 39 | >100 μM | >100 μM | >100 μM | >100 μM |
| N—Ac—CHAVSC—NH$_2$* (#18) | 38 | 52 μM | >100 μM | >100 μM | >100 μM |
| N—Ac—CSHGVC—NH$_2$ (control for #16) | 37 | >100 μM | >100 μM | >100 μM | >100 μM |
| N—Ac—CSHAVC—NH$_2$ (#16) | 36 | >100 μM | >100 μM | >100 μM | >100 μM |
| N—Ac—CAHGVDC—NH$_2$ (control for #22) | 27 | >100 μM | >100 μM | >100 μM | >100 μM |
| N—Ac—CAHAVDC—NH$_2$ (#22) | 26 | >100 μM | >100 μM | >100 μM | >100 μM |
| N—Ac—KHGVD—NH$_2$ (control for #26) | 13 | >100 μM | >100 μM | >100 μM | >100 μM |
| N—Ac—KHAVD—NH$_2$ (#26) | 12 | >100 μM | >100 μM | >100 μM | >100 μM |
| H—CAHGVDC—NH$_2$ (control for #45) | 27 | >100 μM | >100 μM | >100 μM | >100 μM |
| H—CAHAVDC—NH$_2$ (#45) | 26 | >100 μM | >100 μM | >100 μM | >100 μM |
| H—CAHGVDIC—NH$_2$ (control for #47) | 25 | >100 μM | >100 μM | >100 μM | >100 μM |
| H—CAHAVDIC—NH$_2$ (#47) | 24 | >100 μM | >100 μM | >100 μM | >100 μM |
| N—Ac—CVGHC—NH$_2$ (control for #32) | 19 | >100 μM | >100 μM | >100 μM | >100 μM |
| N—Ac—CVAHC—NH$_2$ (#32) | 18 | >100 μM | >100 μM | >100 μM | >100 μM |
| N—Ac—CAHGVDIC—NH$_2$ (control for #14) | 25 | >100 μM | >100 μM | >100 μM | >100 μM |
| N—Ac—CAHAVDIC—NH$_2$ (#14) | 24 | >100 μM | >100 μM | >100 μM | >100 μM |
| N—Ac—CSHGVSSC—NH$_2$ (control for #24) | 43 | >100 μM | >100 μM | >100 μM | >100 μM |
| N—Ac—CSHAVSSC—NH$_2$* (#24) | 42 | 76 μM | >100 μM | >100 μM | >100 μM |

*Incompletely soluble in RPMI at 1 mM

EXAMPLE 5

Chronic Toxicity Study

This Example illustrates a toxicity study performed using a representative cyclic peptide.

Figure 6:
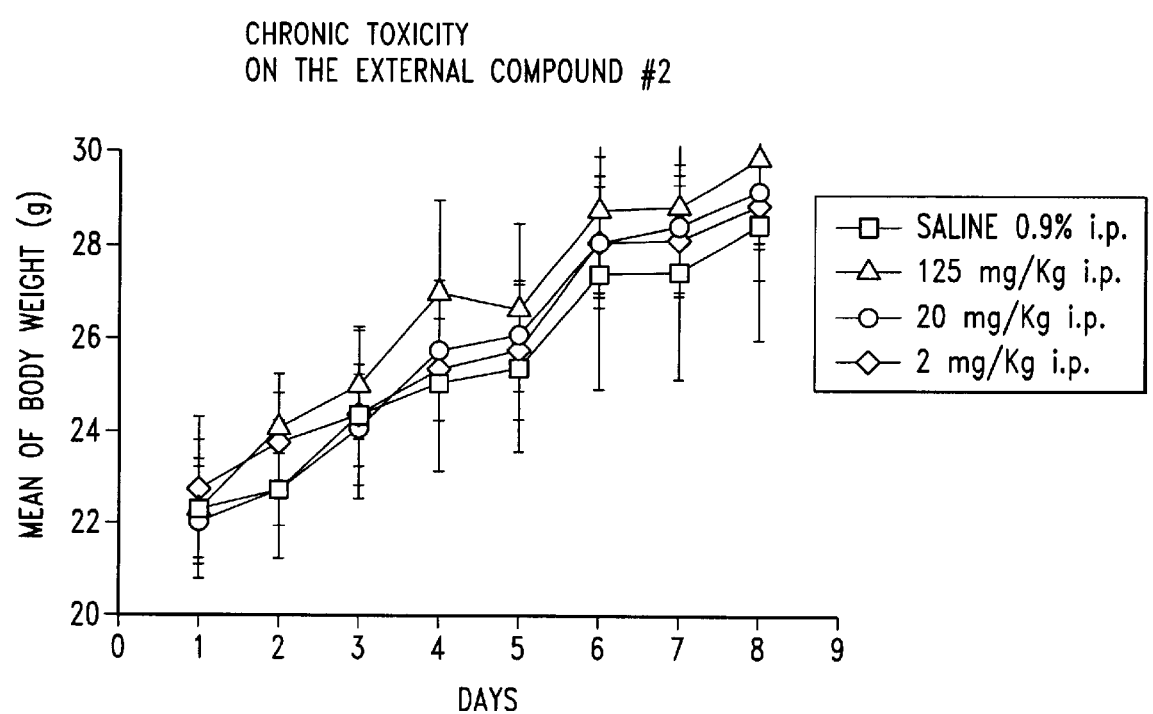

Varying amounts of H-CHAVC-NH$_2$ (SEQ ID NO:10; 2 mg/kg, 20 mg/kg and 125 mg/kg) were injected into mice intraperitoneally every day for three days. During the recovery period (days 4–8), animals were observed for clinical symptoms. Body weight was measured (FIG. 6) and no significant differences occurred. In addition, no clinical symptoms were observed on the treatment or recovery days. Following the four day recovery period, autopsies were performed and no abnormalities were observed.

EXAMPLE 6

Stability of Cyclic Peptide in Blood

This Example illustrates the stability of a representative cyclic peptide in mouse whole blood.

Figure 7:
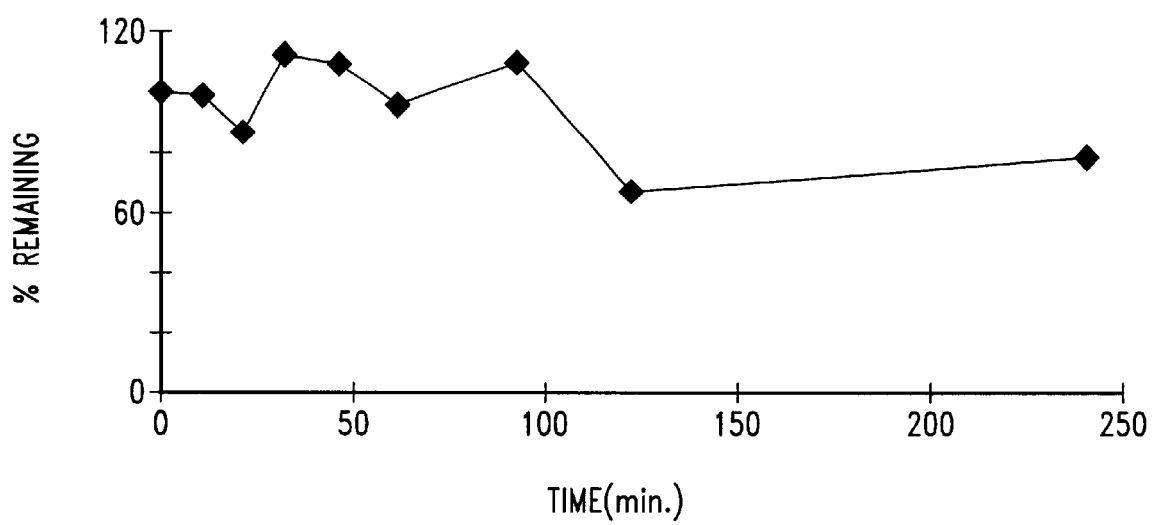

50 μl of a stock solution containing 12.5 μg/ml H-CHAVC-NH$_2$ (SEQ ID NO:10) was added to mouse whole blood and incubated at 37° C. Aliquots were removed at intervals up to 240 minutes, precipitated with acetonitrile, centrifuged and analyzed by HPLC. The results (Table 9 and FIG. 7) are expressed as % remaining at the various time points, and show generally good stability in blood.

TABLE 9

Stability of Representative Cyclic Peptide in Mouse Whole Blood

| Time (Min.) | Area 1 | Area 2 | Average | % Remaining |
|---|---|---|---|---|
| 0 | 341344 | 246905 | 294124.5 | 100.00 |
| 10 | 308924 | 273072 | 290998 | 98.94 |
| 20 | 289861 | 220056 | 254958.5 | 86.68 |
| 30 | 353019 | 310559 | 331789 | 112.81 |
| 45 | 376231 | 270860 | 323545.5 | 110.00 |
| 60 | 373695 | 188255 | 280975 | 95.53 |
| 90 | 435555 | 216709 | 326132 | 110.88 |
| 120 | 231694 | 168880 | 200287 | 68.10 |
| 240 | 221952 | 242148 | 232050 | 78.90 |

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A method for treating spinal cord injuries in a mammal, comprising contacting a neuron at a target site in said mammal by implanting at said site a cell adhesion modulating agent that enhances neurite outgrowth, wherein the modulating agent comprises the sequence His-Ala-Val within a cyclic peptide in which nonadjacent amino acid residues are covalently linked to form a 4–15 amino acid residue peptide ring.

2. A method according to claim 1, wherein the cyclic peptide has the formula:

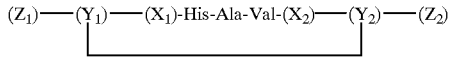

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12;

wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds.

3. A method according to claim 2, wherein $Z_1$ is not present and $Y_1$ comprises an N-acetyl group.

4. A method according to claim 2, wherein $Z_2$ is not present and $Y_2$ comprises a C-terminal amide group.

5. A method according to claim 2, wherein $Y_1$ and $Y_2$ are covalently linked via a disulfide bond.

6. A method according to claim 5, wherein $Y_1$ and $Y_2$ are each independently selected from the group consisting of penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline and derivatives thereof.

7. A method according to claim 5, wherein $Y_1$ and $Y_2$ are cysteine residues or derivatives thereof.

8. A method according to claim 2, wherein $Y_1$ and $Y_2$ are covalently linked via an amide bond.

9. A method according to claim 8, wherein the amide bond is formed is formed between terminal functional groups.

10. A method according to claim 8, wherein the amide bond is formed between residue side-chains.

11. A method according to claim 8, wherein the amide bond is formed between one terminal functional group and one residue side chain.

12. A method according to claim 8, wherein:
(a) $Y_1$ is selected from the group consisting of lysine, ornithine, and derivatives thereof and $Y_2$ is selected from the group consisting of aspartate, glutamate and derivatives thereof; or
(b) $Y_2$ is selected from the group consisting of lysine, ornithine and derivatives thereof and $Y_1$ is selected from the group consisting of aspartate, glutamate and derivatives thereof.

13. A method according to claim 2, wherein $Y_1$ and $Y_2$ are covalently linked via a thioether bond.

14. A method according to claim 2, wherein $Y_1$ and $Y_2$ are each tryptophan or a derivative thereof, such that the covalent bond generates a $\delta_1,\delta_1$-ditryptophan, or a derivative thereof.

15. A method according to claim 1, wherein the modulating agent comprises a sequence selected from the group consisting of HAVC (SEQ ID NO:10), CHAVDC (SEQ ID NO:20), CHAVDIC (SEQ ID NO:50), CHAVDINC (SEQ ID NO:51), CHAVDINGC (SEQ ID NO:76), CAHAVC (SEQ ID NO:22), CAHAVDC (SEQ ID NO:26), CAHAVDIC (SEQ ID NO:24), CRAHAVDC (SEQ ID NO:28), CLRAHAVDC (SEQ ID NO:32), DHAVK (SEQ ID NO:14), KHAVE (SEQ ID NO:16), AHAVDI (SEQ ID NO:34) and derivatives of the foregoing sequences having one or more C-terminal, N-terminal and/or side chain modifications.

16. A method according to claim 1, wherein the modulating agent comprises at least two HAV sequences separated by a linker.

17. A method according to claim 1, wherein the modulating agent is linked to a drug.

18. A method according to claim 1, wherein the modulating agent is linked to a targeting agent.

19. A method according to claim 1, wherein the modulating agent is linked to a solid support.

20. A method according to claim 19, wherein the solid support is a polymeric matrix.

21. A method according to claim 19, wherein the solid support is selected from the group consisting of plastic dishes, plastic tubes, sutures, membranes, ultra thin films, bioreactors and microparticles.

22. A method according to claim 1, wherein the modulating agent is present within a pharmaceutical composition that comprises a pharmaceutically acceptable carrier.

23. A method according to claim 22, wherein the composition further comprises a drug.

24. A method according to claim 22, wherein the cell adhesion modulating agent is present within a sustained-release formulation.

25. A method according to claim 1, wherein the cyclic peptide has the formula:

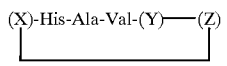

wherein Y is optional and, if present is selected from the group consisting of amino acid residues and combinations thereof in which the residues are linked by peptide bonds, and wherein Y ranges in size from 0 to 10 residues; and wherein X and Z are independently selected from the group consisting of amino acid residues, wherein a disulfide bond is formed between residues X and Z; and wherein X comprises an N-acetyl group.

* * * * *

SEQUENCE LISTING

<160> NUMBER OF SEQ ID NOS: 87

<210> SEQ ID NO 1
<211> LENGTH: 108
<212> TYPE: PRT
<213> ORGANISM: Homo sapiens

<400> SEQUENCE: 1

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
             20                  25                  30

Ser Leu Arg Tyr Ser Val Thr Gly Pro Gly Ala Asp Gln Pro Pro Thr
         35                  40                  45

Gly Ile Phe Ile Leu Asn Pro Ile Ser Gly Gln Leu Ser Val Thr Lys
     50                  55                  60

Pro Leu Asp Arg Glu Gln Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105

<210> SEQ ID NO 2
<211> LENGTH: 108
<212> TYPE: PRT
<213> ORGANISM: Mus musculus

<400> SEQUENCE: 2

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
             20                  25                  30

Ser Leu Arg Tyr Ser Val Thr Gly Pro Gly Ala Asp Gln Pro Pro Thr
         35                  40                  45

Gly Ile Phe Ile Ile Asn Pro Ile Ser Gly Gln Leu Ser Val Thr Lys
     50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                 85                  90                  95

Asn Val Ile Asp Met Asn Asp Asn Arg Pro Glu Phe
                100                 105

<210> SEQ ID NO 3
<211> LENGTH: 108
<212> TYPE: PRT
<213> ORGANISM: Bos taurus

<400> SEQUENCE: 3

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
             20                  25                  30

Ser Leu Arg Tyr Ser Val Thr Gly Pro Gly Ala Asp Gln Pro Pro Thr
         35                  40                  45

```
Gly Ile Phe Ile Ile Asn Pro Ile Ser Gly Gln Leu Ser Val Thr Lys
        50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                     85                  90                  95

Asn Val Ile Asp Met Asn Asp Asn Arg Pro Glu Phe
                100                 105
```

<210> SEQ ID NO 4
<211> LENGTH: 108
<212> TYPE: PRT
<213> ORGANISM: Homo sapiens

<400> SEQUENCE: 4

```
Asp Trp Val Val Ala Pro Ile Ser Val Pro Glu Asn Gly Lys Gly Pro
  1               5                  10                  15

Phe Pro Gln Arg Leu Asn Gln Leu Lys Ser Asn Lys Asp Arg Asp Thr
                 20                  25                  30

Lys Ile Phe Tyr Ser Ile Thr Gly Pro Gly Ala Asp Ser Pro Pro Glu
             35                  40                  45

Gly Val Phe Ala Val Glu Lys Glu Thr Gly Trp Leu Leu Leu Asn Lys
 50                  55                  60

Pro Leu Asp Arg Glu Glu Ile Ala Lys Tyr Glu Leu Phe Gly His Ala
 65                  70                  75                  80

Val Ser Glu Asn Gly Ala Ser Val Glu Asp Pro Met Asn Ile Ser Ile
                 85                  90                  95

Ile Val Thr Asp Gln Asn Asp His Lys Pro Lys Phe
                100                 105
```

<210> SEQ ID NO 5
<211> LENGTH: 108
<212> TYPE: PRT
<213> ORGANISM: Mus musculus

<400> SEQUENCE: 5

```
Glu Trp Val Met Pro Pro Ile Phe Val Pro Glu Asn Gly Lys Gly Pro
  1               5                  10                  15

Phe Pro Gln Arg Leu Asn Gln Leu Lys Ser Asn Lys Asp Arg Gly Thr
                 20                  25                  30

Lys Ile Phe Tyr Ser Ile Thr Gly Pro Gly Ala Asp Ser Pro Pro Glu
             35                  40                  45

Gly Val Phe Thr Ile Glu Lys Glu Ser Gly Trp Leu Leu Leu His Met
 50                  55                  60

Pro Leu Asp Arg Glu Lys Ile Val Lys Tyr Glu Leu Tyr Gly His Ala
 65                  70                  75                  80

Val Ser Glu Asn Gly Ala Ser Val Glu Pro Met Asn Ile Ser Ile
                 85                  90                  95

Ile Val Thr Asp Gln Asn Asp Asn Lys Pro Lys Phe
                100                 105
```

<210> SEQ ID NO 6
<211> LENGTH: 108
<212> TYPE: PRT
<213> ORGANISM: Homo sapiens

<400> SEQUENCE: 6

```
Asp Trp Val Ile Pro Pro Ile Ser Cys Pro Glu Asn Glu Lys Gly Pro
```

```
              1               5                  10                  15
Phe Pro Lys Asn Leu Val Gln Ile Lys Ser Asn Lys Asp Lys Glu Gly
                        20                  25                  30

Lys Val Phe Tyr Ser Ile Thr Gly Gln Gly Ala Asp Thr Pro Pro Val
                35                  40                  45

Gly Val Phe Ile Ile Glu Arg Glu Thr Gly Trp Leu Lys Val Thr Glu
        50                  55                  60

Pro Leu Asp Arg Glu Arg Ile Ala Thr Tyr Thr Leu Phe Ser His Ala
65                  70                  75                  80

Val Ser Ser Asn Gly Asn Ala Val Glu Asp Pro Met Glu Ile Leu Ile
                        85                  90                  95

Thr Val Thr Asp Gln Asn Asp Asn Lys Pro Glu Phe
                100                 105
```

<210> SEQ ID NO 7
<211> LENGTH: 108
<212> TYPE: PRT
<213> ORGANISM: Mus musculus

<400> SEQUENCE: 7

```
Asp Trp Val Ile Pro Pro Ile Ser Cys Pro Glu Asn Glu Lys Gly Glu
 1               5                  10                  15

Phe Pro Lys Asn Leu Val Gln Ile Lys Ser Asn Arg Asp Lys Glu Thr
                        20                  25                  30

Lys Val Phe Tyr Ser Ile Thr Gly Gln Gly Ala Asp Lys Pro Pro Val
                35                  40                  45

Gly Val Phe Ile Ile Glu Arg Glu Thr Gly Trp Leu Lys Val Thr Gln
        50                  55                  60

Pro Leu Asp Arg Glu Ala Ile Ala Lys Tyr Ile Leu Tyr Ser His Ala
65                  70                  75                  80

Val Ser Ser Asn Gly Glu Ala Val Glu Asp Pro Met Glu Ile Val Ile
                        85                  90                  95

Thr Val Thr Asp Gln Asn Asp Asn Arg Pro Glu Phe
                100                 105
```

<210> SEQ ID NO 8
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<220> FEATURE:
<223> OTHER INFORMATION: Description of Unknown Organism: Cadherin
      Calcium Binding Motif

<400> SEQUENCE: 8

```
Asp Xaa Asn Asp Asn
 1               5
```

<210> SEQ ID NO 9
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif

<400> SEQUENCE: 9

Leu Asp Arg Glu

```
1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 10

Cys His Ala Val Cys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 11

Cys His Gly Val Cys
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 12

Lys His Ala Val Asp
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 13

Lys His Gly Val Asp
 1               5
```

```
<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 14

Asp His Ala Val Lys
  1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 15

Asp His Gly Val Lys
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 16

Lys His Ala Val Glu
  1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 17

Lys His Gly Val Glu
  1               5
```

```
<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 18

Cys Val Ala His Cys
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 19

Cys Val Gly His Cys
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 20

Cys His Ala Val Asp Cys
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 21

Cys His Gly Val Asp Cys
  1               5

<210> SEQ ID NO 22
```

```
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 22

Cys Ala His Ala Val Cys
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 23

Cys Ala His Gly Val Cys
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 24

Cys Ala His Ala Val Asp Ile Cys
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 25

Cys Ala His Gly Val Asp Ile Cys
 1               5

<210> SEQ ID NO 26
<211> LENGTH: 7
```

```
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 26

Cys Ala His Ala Val Asp Cys
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 27

Cys Ala His Gly Val Asp Cys
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 28

Cys Arg Ala His Ala Val Asp Cys
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 29

Cys Arg Ala His Gly Val Asp Cys
  1               5

<210> SEQ ID NO 30
<211> LENGTH: 8
<212> TYPE: PRT
```

```
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 30

Cys Leu Arg Ala His Ala Val Cys
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 31

Cys Leu Arg Ala His Gly Val Cys
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 32

Cys Leu Arg Ala His Ala Val Asp Cys
  1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 33

Cys Leu Arg Ala His Gly Val Asp Cys
  1               5

<210> SEQ ID NO 34
<211> LENGTH: 6
<212> TYPE: PRT
<213> ORGANISM: Artificial Sequence
```

```
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 34

Ala His Ala Val Asp Ile
  1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 35

Ala His Gly Val Asp Ile
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 36

Cys Ser His Ala Val Cys
  1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 37

Cys Ser His Gly Val Cys
  1               5

<210> SEQ ID NO 38
<211> LENGTH: 6
<212> TYPE: PRT
<213> ORGANISM: Artificial Sequence
<220> FEATURE:
```

```
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 38

Cys His Ala Val Ser Cys
  1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 39

Cys His Gly Val Ser Cys
  1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 40

Cys Ser His Ala Val Ser Cys
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 41

Cys Ser His Gly Val Ser Cys
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Cyclic
```

```
       peptide with classical cadherin cell adhesion
       recognition sequence
<220> FEATURE:
<223> OTHER INFORMATION: Cyclic Peptide may comprise N-terminal
       modification such as acetyl or alkoxybenzyl group
       and/or C-terminal modifications such as amide or
       ester group

<400> SEQUENCE: 42

Cys Ser His Ala Val Ser Ser Cys
 1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:  Cyclic
       control peptide
<220> FEATURE:
<223> OTHER INFORMATION: Cyclic Peptide may comprise N-terminal
       modification such as acetyl or alkoxybenzyl group
       and/or C-terminal modifications such as amide or
       ester group

<400> SEQUENCE: 43

Cys Ser His Gly Val Ser Ser Cys
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence:  Cyclic
       peptide with classical cadherin cell adhesion
       recognition sequence
<220> FEATURE:
<223> OTHER INFORMATION: Cyclic Peptide may comprise N-terminal
       modification such as acetyl or alkoxybenzyl group
       and/or C-terminal modifications such as amide or
       ester group

<400> SEQUENCE: 44

Cys His Ala Val Ser Ser Cys
 1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence:  Cyclic
       control peptide
<220> FEATURE:
<223> OTHER INFORMATION: Cyclic Peptide may comprise N-terminal
       modification such as acetyl or alkoxybenzyl group
       and/or C-terminal modifications such as amide or
       ester group

<400> SEQUENCE: 45

Cys His Gly Val Ser Ser Cys
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:  Cyclic
       peptide with classical cadherin cell adhesion
```

```
        recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 46

Ser His Ala Val Ser Ser
  1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 47

Ser His Gly Val Ser Ser
  1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 48

Lys Ser His Ala Val Ser Ser Asp
  1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence:  Cyclic
      control peptide
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 49

Lys Ser His Gly Val Ser Ser Asp
  1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
```

```
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 50

Cys His Ala Val Asp Ile Cys
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 51

Cys His Ala Val Asp Ile Asn Cys
 1               5

<210> SEQ ID NO 52
<211> LENGTH: 5
<212> TYPE: PRT
<213> ORGANISM: Unknown
<220> FEATURE:
<223> OTHER INFORMATION: Description of Unknown Organism:  Cadherin cell
      adhesion recognition sequencebound by
      alpha-6-beta-1 integrin

<400> SEQUENCE: 52

Tyr Ile Gly Ser Arg
 1               5

<210> SEQ ID NO 53
<211> LENGTH: 10
<212> TYPE: PRT
<213> ORGANISM: Unknown
<220> FEATURE:
<223> OTHER INFORMATION: Description of Unknown Organism:  Cadherin cell
      adhesion recognition sequence bound by N-CAM

<400> SEQUENCE: 53

Lys Tyr Ser Phe Asn Tyr Asp Gly Ser Glu
 1               5                  10

<210> SEQ ID NO 54
<211> LENGTH: 17
<212> TYPE: PRT
<213> ORGANISM: Unknown
<220> FEATURE:
<223> OTHER INFORMATION: Description of Unknown Organism:  N-CAM heparin
      sulfate binding site

<400> SEQUENCE: 54

Ile Trp Lys His Lys Gly Arg Asp Val Ile Leu Lys Lys Asp Val Arg
 1               5                  10                  15

Phe

<210> SEQ ID NO 55
<211> LENGTH: 4
```

```
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 55

Ile Asp Asp Lys
  1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 56

Asp Asp Lys Ser
  1

<210> SEQ ID NO 57
<211> LENGTH: 9
<212> TYPE: PRT
<213> ORGANISM: Unknown
<220> FEATURE:
<223> OTHER INFORMATION: Description of Unknown Organism:  Nonclassical
      cadherin cell adhesion recognition sequence
<220> FEATURE:
<221> NAME/KEY: MOD_RES
<222> LOCATION: (1)
<223> OTHER INFORMATION: Where Xaa is an independently selected amino
      acid residue
<220> FEATURE:
<221> NAME/KEY: MOD_RES
<222> LOCATION: (3)
<223> OTHER INFORMATION: Where Xaa is an independently selected amino
      acid residue
<220> FEATURE:
<221> NAME/KEY: MOD_RES
<222> LOCATION: (4)
<223> OTHER INFORMATION: Where Xaa is Isoleucine, Leucine or Valine
<220> FEATURE:
<221> NAME/KEY: MOD_RES
<222> LOCATION: (5)
<223> OTHER INFORMATION: Where Xaa is Aspartic Acid, Asparagine or
      Glutamic Acid
<220> FEATURE:
<221> NAME/KEY: MOD_RES
<222> LOCATION: (6)..(7)
<223> OTHER INFORMATION: Where Xaa is an independently selected amino
      acid residue
<220> FEATURE:
<221> NAME/KEY: MOD_RES
<222> LOCATION: (8)
<223> OTHER INFORMATION: Where Xaa is Serine, Threonine or Asparagine

<400> SEQUENCE: 57

Xaa Phe Xaa Xaa Xaa Xaa Xaa Xaa Gly
  1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 58

Val Ile Asp Asp Lys
  1
```

```
<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 59

Ile Asp Asp Lys Ser
  1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 60

Val Ile Asp Asp Lys Ser
  1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 61

Asp Asp Lys Ser Gly
  1

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence:
      Synthesized Peptide
<220> FEATURE:
<221> NAME/KEY: MOD_RES
<222> LOCATION: (1)
<223> OTHER INFORMATION: BLOCKED by 9-fluorenymethyloxycarbonyl
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-Butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
```

```
<223> OTHER INFORMATION: Methoxy terminal group

<400> SEQUENCE: 62

Cys Asp Gly Tyr Pro Lys Asp Cys Lys Gly
  1               5                  10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence:
      Synthesized Cyclic Peptide
<220> FEATURE:
<221> NAME/KEY: MOD_RES
<222> LOCATION: (1)
<223> OTHER INFORMATION: 9-fluorenylmethoxycarbonyl protecting group
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
<223> OTHER INFORMATION: Methoxy terminal group

<400> SEQUENCE: 63

Cys Asp Gly Tyr Pro Lys Asp Cys Lys Gly
  1               5                  10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence:
      Synthesized peptide
<220> FEATURE:
<221> NAME/KEY: MOD_RES
<222> LOCATION: (1)
<223> OTHER INFORMATION: Residue has t-butoxycarbonyl, and Trityl or
      Acetamidomethyl protecting groups
<220> FEATURE:
<221> NAME/KEY: MOD_RES
<222> LOCATION: (5)..(6)
<223> OTHER INFORMATION: tert-butyl protecting group
<220> FEATURE:
<221> NAME/KEY: MOD_RES
<222> LOCATION: (7)
<223> OTHER INFORMATION: Trityl or acetaminomethly protecting group

<400> SEQUENCE: 64

Cys Gly Asn Leu Ser Thr Cys Met Leu Gly
  1               5                  10

<210> SEQ ID NO 65
<211> LENGTH: 10
```

```
<212> TYPE: PRT
<213> ORGANISM: Artificial Sequence
<220> FEATURE:
<223> OTHER INFORMATION: Description of Artificial Sequence:
      Synthesized cyclic peptide
<220> FEATURE:
<221> NAME/KEY: MOD_RES
<222> LOCATION: (1)
<223> OTHER INFORMATION: t-butoxycarbonyl protecting group
<220> FEATURE:
<221> NAME/KEY: MOD_RES
<222> LOCATION: (5)..(6)
<223> OTHER INFORMATION: tert-butyl protecting group

<400> SEQUENCE: 65

Cys Gly Asn Leu Ser Thr Cys Met Leu Gly
 1               5                  10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence:
      Synthesized peptide
<220> FEATURE:
<221> NAME/KEY: MOD_RES
<222> LOCATION: (2)
<223> OTHER INFORMATION: Residue has Acetamidomethyl or
      tert-Acetaminomethyl or tert-butyl protecting
      group
<220> FEATURE:
<221> NAME/KEY: MOD_RES
<222> LOCATION: (6)
<223> OTHER INFORMATION: Residue has Acetamidomethyl,
      tert-Acetamidomethyl or tert-butyl protecting group
<220> FEATURE:
<221> NAME/KEY: MOD_RES
<222> LOCATION: (9)
<223> OTHER INFORMATION: AMIDATION

<400> SEQUENCE: 66

Cys Tyr Ile Gln Asn Cys Pro Leu Gly
 1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence:
      Synthesized cyclic peptide
<220> FEATURE:
<221> NAME/KEY: MOD_RES
<222> LOCATION: (9)
<223> OTHER INFORMATION: AMIDATION

<400> SEQUENCE: 67

Cys Tyr Ile Gln Asn Cys Pro Leu Gly
 1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
```

```
      ester group
<220> FEATURE:
<221> NAME/KEY: MOD_RES
<222> LOCATION: (5)
<223> OTHER INFORMATION: Where Xaa is beta,beta-dimethyl cysteine

<400> SEQUENCE: 68

Cys His Ala Val Xaa
  1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-tetramethylene cysteine

<400> SEQUENCE: 69

Ile Xaa Tyr Ser His Ala Val Ser Cys Glu
  1               5                  10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-pentamethylene cysteine

<400> SEQUENCE: 70

Ile Xaa Tyr Ser His Ala Val Ser Ser Cys
  1               5                  10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (1)
<223> OTHER INFORMATION: Where Xaa is beta-mercaptopropionic acid

<400> SEQUENCE: 71
```

-continued

```
Xaa Tyr Ser His Ala Val Ser Ser Cys
  1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (1)
<223> OTHER INFORMATION: Where Xaa is
      beta,beta-pentamethylene-beta-mercaptopropionic
      acid

<400> SEQUENCE: 72

Xaa Tyr Ser His Ala Val Ser Ser Cys
  1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<221> NAME/KEY: MOD_RES
<222> LOCATION: (4)
<223> OTHER INFORMATION: Where Serine is D-Serine

<400> SEQUENCE: 73

His Ala Val Ser Ser
  1               5

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence:
      Synthesized cyclic peptide

<400> SEQUENCE: 74

Trp Gly Gly Trp
  1

<210> SEQ ID NO 75
<211> LENGTH: 15
<212> TYPE: PRT
<213> ORGANISM: Homo sapiens
<220> FEATURE:
<223> OTHER INFORMATION: Description of Artificial Sequence:
      Representative immunogen containing the HAV
      classical cadherin cell adhesion recognition
      sequence
<220> FEATURE:
<223> OTHER INFORMATION: N-cadherin with HAV cell adhesion recognition
      sequence and flanking amino acids

<400> SEQUENCE: 75
```

Phe His Leu Arg Ala His Ala Val Asp Ile Asn Gly Asn Gln Val
 1               5                   10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 76

Cys His Ala Val Asp Ile Asn Gly Cys
 1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 77

Ile Asp Asp Lys Ser Gly
 1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 78

Val Ile Asp Asp Lys Ser Gly
 1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence:  Peptide
      with classica l cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 79

Leu Arg Ala His Ala Val Asp Ile Asn Gly
 1               5                   10

<210> SEQ ID NO 80
<211> LENGTH: 14
<212> TYPE: PRT
<213> ORGANISM: Homo sapiens
<220> FEATURE:
<223> OTHER INFORMATION: N-cadherin with HAV cell adhesion recognition
      sequence and flanking amino acids

```
<400> SEQUENCE: 80

Arg Phe His Leu Arg Ala His Ala Val Asp Ile Asn Gly Asn
 1               5                  10

<210> SEQ ID NO 81
<211> LENGTH: 12
<212> TYPE: PRT
<213> ORGANISM: Homo sapiens
<220> FEATURE:
<223> OTHER INFORMATION: E-cadherin with HAV cell adhesion recognition
      sequence and flanking amino acids

<400> SEQUENCE: 81

Thr Leu Phe Ser His Ala Val Ser Ser Asn Gly Asn
 1               5                  10

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Peptide
      comprising an OB-cadherin cell adhesion recognition sequence

<400> SEQUENCE: 82

Phe Val Ile Asp Asp Lys
 1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Peptide
      comprising an OB-cadherin cell adhesion recognition sequence

<400> SEQUENCE: 83

Phe Val Ile Asp Asp Lys Ser
 1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Peptide
      comprising an OB-cadherin cell adhesion recognition sequence

<400> SEQUENCE: 84

Phe Val Ile Asp Asp Lys Ser Gly
 1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Peptide
      comprising an OB-cadherin cell adhesion recognition sequence

<400> SEQUENCE: 85

Ile Phe Val Ile Asp Asp Lys
 1               5

<210> SEQ ID NO 86
<211> LENGTH: 8
```

-continued

```
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 86

Ile Phe Val Ile Asp Asp Lys Ser
  1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence:  Peptide
      comprising an OB-cadherin cell adhesion recognition sequence

<400> SEQUENCE: 87

Ile Phe Val Ile Asp Asp Lys Ser Gly
  1               5
```